(12) United States Patent
Bokelmann et al.

(10) Patent No.: US 7,780,340 B2
(45) Date of Patent: Aug. 24, 2010

(54) CHEESE VAT HAVING FLUID ACCESSIBLE SEAL ASSEMBLY

(75) Inventors: Paul R. Bokelmann, Fond du Lac, WI (US); Craig J. Campbell, Waverly, MN (US); Gary L. Starkson, Lester Prairie, MN (US)

(73) Assignee: Advanced Process Technologies, Inc., Cokato, MN (US)

( * ) Notice: Subject to any disclaimer, the term of this patent is extended or adjusted under 35 U.S.C. 154(b) by 934 days.

(21) Appl. No.: 11/565,211

(22) Filed: Nov. 30, 2006

(65) Prior Publication Data

US 2008/0131313 A1    Jun. 5, 2008

(51) Int. Cl.
*F16J 15/32* (2006.01)
*F16J 15/34* (2006.01)

(52) U.S. Cl. .................. 366/331; 277/402; 277/407

(58) Field of Classification Search ................. 366/331; 277/402, 407, 358, 571
See application file for complete search history.

(56) References Cited

U.S. PATENT DOCUMENTS

| | | | |
|---|---|---|---|
| 62,785 A | 3/1867 | Tambling | |
| 299,685 A | 6/1884 | Schwarzschild | |
| 568,664 A | 9/1896 | Cripe | |
| 592,708 A | 10/1897 | Howe | |
| 1,156,050 A | 10/1915 | Brierley | |
| 1,525,394 A | 2/1925 | Jolicoeur | |
| 2,521,890 A * | 9/1950 | Alexander | 324/102 |
| 3,751,010 A | 8/1973 | Latinen | |
| 4,108,058 A | 8/1978 | Sjoholm et al. | |
| 4,136,886 A * | 1/1979 | Sjoholm et al. | 277/402 |
| 4,861,044 A | 8/1989 | Jay | |
| 4,952,069 A | 8/1990 | Boulard | |
| 4,989,504 A | 2/1991 | Jay | |
| 5,004,440 A | 4/1991 | Suzuki | |
| 5,753,282 A | 5/1998 | Tortosa | |
| 5,951,022 A | 9/1999 | Gorman et al. | |
| 6,082,889 A | 7/2000 | Tortosa | |

\* cited by examiner

*Primary Examiner*—Tony G Soohoo
(74) *Attorney, Agent, or Firm*—Moore & Hansen, PLLP

(57) ABSTRACT

A cheese process vat is disclosed. The cheese process vat includes an enclosure and a shaft assembly, preferably a shaft assembly having a shaft and a plurality of agitator panels arranged on the shaft. The cheese process vat preferably further includes a shaft seal assembly having a fluid accessible clean-in-place chamber. Methods of using the respective cheese process vats are also disclosed.

23 Claims, 12 Drawing Sheets

CHEESE VAT HAVING FLUID ACCESSIBLE SEAL ASSEMBLY

BACKGROUND OF THE DISCLOSURE

1. Field of the Invention

The present invention relates to a cheese process vat. More specifically, the present invention relates to a cheese process vat including a shaft seal assembly having a fluid accessible clean-in-place chamber. In yet another embodiment, the present invention relates to a method of cleaning/sanitizing an interior of a cheese process vat.

2. Description of the Related Art

In the 1970's, a number of companies manufactured enclosed vertically agitator shafted vats for making cheese and cheese-like products. These enclosed vats improved upon inconsistent cheese making results generally noted in the open cheese making vats that were common in those days. The enclosed vats also reduced the risk of foreign material contamination and the interior could be automatically cleaned with automatic, clean-in-place (CIP) spray systems. Initially, these vats had vertical agitator shafts. Such vats include the Damrow® Double O™ Vat and the Stoelting® Vertical Vat.

In the late 1980's, cheese process vats having horizontal agitator shafts were introduced. Known horizontal agitator shaft cheese process vats, such as that disclosed by Jay (U.S. Pat. No. 4,989,504), are dual horizontal agitator shaft cheese process vats that are believed to provide considerably improved product yields as compared to the prior vertically agitator shafted vats.

Cheese process vats have also been made having a single horizontal agitator shaft. Previous cheese process vats having single horizontal agitator shafts typically have a majority of their blade clusters or agitator panels on one side of the agitator shaft with blade panels generally confined to about 1000 or less of the full 360° radius of the agitator shaft, creating a substantially unbalanced weight distribution with respect to the placement of the agitator panels within the agitator shaft assembly. Such vats include the Tebel OST, the Wincanton and the Stoelting single agitator shaft cheese process vats.

In these vats, during the initial stages of cutting the coagulum, the entire mass of coagulum has a tendency to rotate with the agitator shaft assembly. To compensate for this rolling/rotating action, it is usually necessary to increase the speed of the agitator shaft assembly, which is believed to negatively influence yield, by shattering the coagulum, thus allowing fat release and creation of cheese fines that are drained out of the curd with the whey when the whey is separated from the cheese curds. Further, if a horizontal agitator shaft assembly has a substantially unbalanced weight distribution with respect to the placement of the agitator panels along the agitator shaft, the motor, speed reducer and bearings experience uneven loads as the agitator shaft rotates. The loading along the shaft will generally alternate from a high positive load to one that might be called a free fall, regenerative or negative load. This can cause uneven wear and premature failure of the above mentioned parts.

Known methods of attaching blade clusters or agitator panels to the agitator shaft include welding the agitator panels to stubs located on the main agitator shaft. The blunt edges of the stubs during the cutting phase can damage the coagulum enough to negatively affect product yield.

The original enclosed cheese making vats employed vertical agitator shafts and therefore, did not require a sophisticated water-tight and sanitary seal assembly. The agitator shaft came through an opening in the top of the vessel, which was always above the level of the liquid. With the advent of cheese making vats with horizontal agitator shafts, however, it became necessary to seal the agitator shaft so milk or product would not leak as both ends of the agitator shaft are typically below liquid level during cheese making operations. Under rules promulgated by the USDA, it also became necessary to provide a suitable system to clean the seal assembly and, as further required by the USDA, provide a leak detection port which is open to the floor during the production of cheese. Existing cheese process vat seals consist of a combination shaft seal and face seal molded into one unit such as that disclosed by Jay (U.S. Pat. No. 4,861,044). Typically, the cleaning/sanitizing solution is pumped, through a hole that is molded into the seal between the shaft seal and the face seal.

Testing and evaluating the cheese making performance is contingent on the cheese making process. The cheese making process is made up of numerous steps that change for each type of cheese. Cheese making steps generally include, but are not limited to the following:

First, the sanitized vat is filled with fluid milk and combined with other cheese constituents like calcium, a starter culture a rennet solution and a coloring agent. As the cheese process vat is filling, the agitator shaft assembly automatically starts agitating the fluid milk when the milk fill weight reaches a first stir set point. During the "fill" step, other actions take place, including heating the milk in the vat body, if the milk temperature is not at a required set point.

To add any desired coloring agent, appropriate valves are opened and a color pump generally starts to add a coloring agent, preferably annatto, to the milk when the milk fill weight reaches a preset point. The coloring agent is metered into the milk.

When the milk fill weight reaches another preset point, another set of valves are opened and a pump begins to pump a starter culture into the milk. The starter is generally a bacterial culture in a medium such as milk that is added to enhance flavor and lower pH. Food colorings, calcium and the like may also be added at this point.

Once the vat is full of fluid milk, a modern, programmed cheese process vat will generally advance to a "stir" step commonly referenced as a "rennet stir" step. Rennet solutions include proteolytic enzymes that promote coagulation of the milk when the enzymes react with casein micelles to produce casein proteins that bind together to form a coagulum that is a protein matrix in which a portion of the milk fat is retained. Once the operator is aware of the appropriate time to add the rennet solution and operator initiates a programmed addition sequence, the agitator shaft will generally ramp up to a programmed agitation speed in a stir mode.

Known methods of introducing the rennet solution are known to include manual addition using a pail from the top of the vat, spraying over the top of the surface of the milk using spray nozzles or a gravity feed orifice from an overhead manifold.

Following the addition of the rennet solution, the agitator shaft assembly rotation speed is generally increased to a further programmed speed in the stir mode/direction to thoroughly mix the rennet into the fluid milk. In an attempt to obtain a homogeneous mixture, in which the rennet is evenly distributed to every part of the fluid milk within the vat body, the contents of the vat are often agitated aggressively. This can be counter productive, however, as the coagulum may not set as well under such conditions. After this step is timed out, the cheese process vat advances to an "anti-swirl" step in which the direction of the rotation of the agitator panels is reversed.

The "anti-swirl" step helps to slow down the action of the milk rotating in one direction. The agitator shaft assembly will then begin a cut mode at high RPMs and gradually reduce the agitating speed until stopped. After this step is timed out, the cheese process vat advances to a "set" step in which the casein matrix is allowed to set or coagulate.

The agitator shaft assembly does not rotate in the "set" step. In the "set" step, the milk protein coagulates while the agitator shaft assembly idles to permit the coagulum to form. After the programmed set time expires, the operator will check the set. When the set is ready, the operator will initiate a series of "cut" steps.

In the "cut" steps, the agitator shaft assembly gradually ramps up to a programmed speed in which the coagulum is cut into individual cheese curd matrices (cheese curd). After these steps are timed out, the cheese process vat advances to a "heal" step.

In the "heal" step, the agitator shaft assembly does not rotate. This step allows the outer skin or "shell" of the curd to develop in order to reduce "bleeding" of fat and moisture from the curd. After this step is timed out, the cheese process vat advances to a "forwork" step.

In the "forwork" step, the agitator shaft ramps up in a selected cut or stir mode. In this step, the curd is gently stirred at a relatively slow agitation speed. After this step is timed out, the cheese process vat advances to a "cooking" step.

In the "cooking" step, the agitator shaft assembly increases up to a programmed speed in the stir or cut direction. A vat steam shut off valve or hot water shut off valve generally opens to permit steam or hot water to circulate in the outer jacket surrounding the interior of the vat body. An intermittent agitating time parameter is available to help keep curd from knitting together at low agitator shaft assembly speeds. The "cooking" step will not advance until both the time and temperature required by the program are met. The cheese process vat will then advance to a "predraw/settle" step once cooking is complete.

In the "predraw/settle" step, the agitator shaft assembly does not run. The agitator shaft assembly is parked in a vertical position. Curd gradually drops into the whey fluid mixture in the vat body because it is denser than the whey that remains after the cheese curd is formed. After this step is timed out, the cheese process vat advances to a "predraw" step.

In the "predraw" step, the agitator shaft assembly does not run as it remains parked in the vertical position. A predraw valve opens and a predraw pump starts to remove whey from the vat body. Once a set amount of whey is drawn off, the predraw pump shuts off and the predraw valve closes.

Next, during an "end stir" step, the agitator shaft assembly increases to a programmed speed in the stir direction. The "end stir" step ends and a "curd transfer" step begins once the programmed time for the "end stir" step has elapsed.

Finally, in the "curd transfer" step, appropriate valves are opened and curd pumps will pump the curd and any remaining whey out of the vat body to finishing areas. During the curd transfer, the agitator shaft assembly speed increases and has the option to be in a "stir" mode or a "cut" mode.

Once empty, the interior of the vat is usually cleaned automatically with the use of internally mounted spray devices that are part of a sanitizing system generally called a "clean in place" (CIP) system.

Although cheese making has advanced significantly in the past 20 to 30 years, it will be appreciated that a cheese process vat that increases cheese yield is needed in order to make automated cheese making more efficient and less reliant upon operators that possess the knowledge of the "art" of cheese making. What is also needed is a cheese process vat that is easier to clean, easier to operate without undue wear on parts and easier to operate in ways that produce cheese more efficiently. What is further needed is a cheese process vat with a shaft seal assembly that is easily adjustable.

SUMMARY OF THE DISCLOSURE

The cheese process vat of the present invention preferably includes a cylindrical vat body having an interior that is substantially horizontal and sized appropriately to contain a resulting product. Preferred cheese process vats of the present invention further include a single, generally horizontal agitator shaft with agitator panels including blades that have two distinct functions. While rotating in one rotational direction, sharp edges on the blades cut the coagulum. For stirring operations, rotating the agitator shaft in the opposite direction, unsharpened edges of the blades stir the mixture without additional cutting.

The present invention further includes a unique arrangement of the agitator panels. In preferred embodiments, the agitator panels are substantially balanced along an axis of the agitator shaft in a generally planar fashion. Substantially balanced agitator panels provide uniform or even wear on parts, like motor parts, speed reducer parts, variable frequency drive parts and the like. This wear reduction minimizes lost production time and product loss due to mid-cycle vat breakdowns caused by premature failure of the previously mentioned parts.

The agitator shaft assembly of the present invention preferably further includes disk-like collars that are welded to the agitator shaft while the agitator shaft is external to the vat body. If necessary, the agitator shaft can be straightened at that time with known methods and techniques. After installation of the straightened agitator shaft, the agitator panels are welded to the outer diameter of the disk-like collars. Welding to the outer diameter of the disk-like collars virtually eliminates any agitator shaft distortion caused by heat generated during the welding process. In addition, the disk-like collar is believed to be gentler on the coagulum when the agitator shaft rotates because the number of blunt edges being forced through the coagulum is minimized.

The blade clusters or agitator panels preferably have of a pair of thick, radially positioned primary blades attached to the collar, thinner secondary blades attached to the primary blades and parallel to a centerline of the agitator shaft and a set of radially arrayed tertiary blades, which are also thin blades, attached to the secondary blades. A complete agitator shaft assembly has multiple agitator clusters positioned to provide a substantially balanced assembly preferably arrayed in a single plane through the centerline of the agitator shaft. This substantially balanced array will preferably have substantial balance with respect to either or both of the surface area of the respective agitator panels arrayed on the respective opposite sides of the agitator shaft or the weight of the respective agitator panels arrayed on the respective opposite sides of the agitator shaft.

Additionally, the cheese process vat of a further embodiment of the present invention further includes an injection nozzle assembly, even more preferably, a plurality of injection nozzle assemblies. Each injection nozzle assembly can inject a stream of a rennet solution through the surface of the fluid milk within the vat body well below the surface of the fluid milk, thereby providing a more effective distribution of the rennet solution. This process of injecting the rennet mixture below the surface of the fluid milk improves the cheese making process by incorporating the aqueous rennet solution into the milk faster, more pervasively and more effectively. An effective incorporation of the rennet solution will create coagulation that is substantially uniform throughout the fluid milk thereby increasing yield.

The improved cheese process vat of a further embodiment of the present invention further includes an adjustable shaft seal assembly. Because the agitator shaft is secured in the vat body below the operating liquid level, a shaft seal of some sort will be necessary to prevent the contents of the cheese process vat from leaking through the joint between the seal assembly and the agitator shaft. Since a cheese process vat is subject to regulatory scrutiny, the shaft seal assembly also has to be easily cleanable and provide a leak detection port. The shaft seal assembly preferably includes a seal assembly subunit including an inner seal holder, a face seal and a separate shaft seal, each of which surround and are concentric with the agitator shaft; wherein the shaft seal and the face seal are engaged with and separated by the inner seal holder. The face seal and the shaft seal each have a seal body and a seal lip. The face seal lip extends away from the face seal body and is pre-loaded such that the face seal lip engages an inner face of the agitator shaft. The shaft seal lip extends away from the shaft seal body and is pre-loaded so that the shaft seal lip engages the agitator shaft. The inner seal holder defines a first portion of a fluid conduit channel and the agitator shaft, the inner seal holder, the face seal and the shaft seal cooperate to define a fluid accessible cleaning chamber to which cleaning fluid can flow via a fluid conduit channel that leads to the exterior of the vat.

As mentioned above, the adjustable seal assembly of a further embodiment of the present invention is preferably pre-loaded against the inner face of a concentric flange of the agitator shaft having a wear disk. The face seal lip and a shaft seal lip are designed and configured to act as check valves where liquid can pass in one direction only when under pressure, unless the seals fail. When the interior of the vat body is being cleaned and when the appropriate flow control valves are actuated, cleaning/sanitizing solution is allowed to flow into the chamber and because the shaft seal lip is designed to be angled toward the chamber, it stays closed and prevents the solution from leaking out into the joint between the agitator shaft and shaft seal assembly. Since the face seal lip is angled away from the chamber, the face seal lip actually opens up as the solution flows under pressure into the chamber, thus cleaning the chamber and the backside of the face seal lip. The seal assembly of the present invention preferably aids in detecting leaks due to the failure of the face seal. While in use, the face seal is positioned so that any leakage of milk or whey into the chamber from the interior of the vat body will leak onto the floor from the fluid conduit channel, providing a visual indicator to the operator that the face seal has failed and that seal maintenance is needed.

In preferred embodiments of the present cheese process vat the face seal may be adjusted without having to enter the vat body and without having to take the seal assembly apart and rebuild it. To adjust the face seal, the user simply loosens the external fasteners holding the seal assembly together and removes at least one shim from each fastener, then retightens the respective fasteners. The shims provide an easy way to adjust or increase lip pressure against the inner face of inner face wear plate.

Thus, it is an object of the present invention to provide a cheese process vat having a horizontal agitator shaft having substantially balanced agitator panels in both surface area and weight.

Thus, it is another object of the present invention to provide a cheese process vat having at least one injection nozzle assembly to inject rennet solution during the cheese making process.

Thus, it is yet another object of the present invention to provide a cheese process vat having an easily adjustable shaft seal assembly that includes a fluid accessible cleaning chamber.

These and other objects and advantages of the invention will appear more fully from the following description, made in conjunction with the accompanying drawings wherein like reference characters refer to the same or similar parts throughout the several views. And, although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention, which is defined by the claims.

BRIEF DESCRIPTION OF THE DRAWINGS

In the drawings, in which corresponding reference numerals and letters indicate corresponding parts of the various embodiments throughout the several views, and in which the various embodiments generally differ only in the manner described and/or shown, but otherwise include corresponding parts;

FIG. 1A is a schematic plan view of the cheese process vat shown in FIG. 1;

DETAILED DESCRIPTION OF THE PREFERRED EMBODIMENTS

Figure 1:
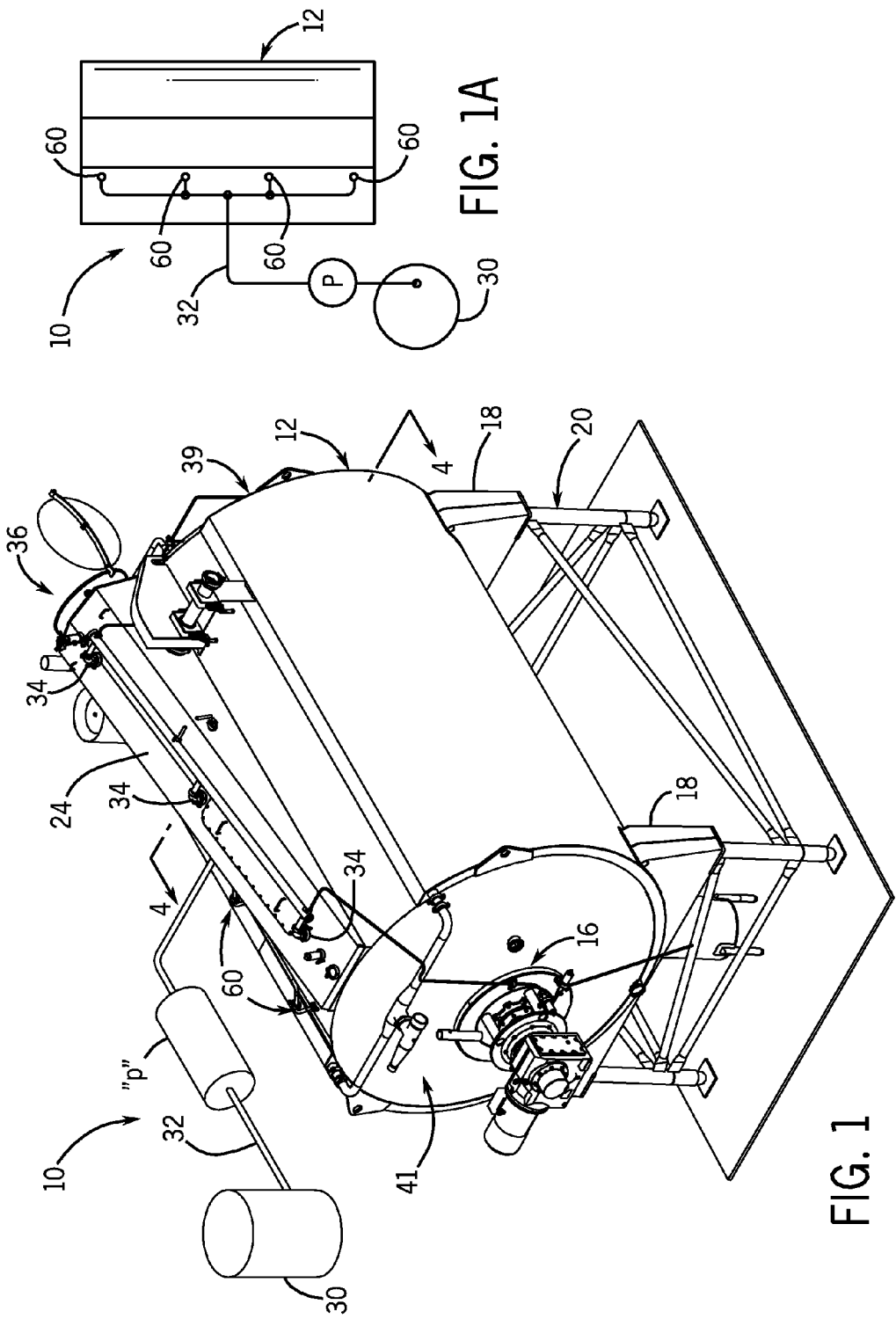
FIG. 1 is an elevated perspective view of a preferred cheese process vat of the present invention.

Referring now to the drawings and to FIGS. 1-13 in particular, FIG. 1 illustrates a preferred cheese process vat 10 of the present invention. The cheese process vat 10 has an enclosure or vat body 12 having an interior 28 (see FIGS. 3-6A), an agitator shaft assembly 14 (see FIGS. 3, 4, 6A and 6B) and a seal assembly 16, which is best illustrated in detail in FIGS. 10-13. The agitator shaft assembly 14 includes a hollow stainless steel agitator shaft 40 that extends between the respective ends 39, 41 of the vat body 12.

The cheese process vat 10 is supported by a set of cradles 18 resting on a support frame assembly 20. Preferably, the support frame assembly 20 and cradles 18 support the vat body 12 at an angle or tilt away from the horizontal such that contents of the cheese process vat 10 will drain completely with relative ease through a drainage port 22 (see FIG. 6A). The preferred cheese process vat 10 of the present invention further comprises a roof 24 on the top of the vat body 12. The shape of the roof 24 corresponds to a vat access opening 26 in the vat body 12 (see FIG. 2 in particular) and provides an area where someone may access the interior 28 of the vat body 12 (see FIG. 3) prior to completion of the cheese process vat 10 of the present invention in which the roof 24 is preferably welded to the vat body 12 proximate the vat access opening 26. Once the roof 24 is welded to the vat body 12, the only way for a person to get into the interior 28 is to enter via a personnel access port or "manway" 36.

The manway 36 is an important access portal for entrance into the interior 28 of the vat body 12 during completion of the assembly of a cheese process vat 10 of the present invention, because the agitator shaft assembly 14 will be completed inside the interior 28 when agitator panels or blade clusters 42a, 42b, 42c are passed into the interior 28, via a roof opening 37 in the roof 24, so that the agitator panels 42a, 42b, 42c can be welded onto the agitator shaft 40. In preferred embodiments, the blade clusters 42a, 42b, 42c are welded to disk-like collars 76, which were in turn welded to the hollow agitator shaft 40 before the agitator shaft is introduced into the interior 28 of the vat body 12. Because the heat generated during welding procedures can cause an agitator shaft 40 to become warped or to develop an irregular axis about which it will be forced to rotate, welding the collars 76 to the agitator shaft 40 outside of the interior 28 is advantageous because of the greater availability of the counter measures to address the effects of heat on the straightness of the agitator shaft 40. Once the collars 76 are welded to the agitator shaft 40, and the agitator shaft is straightened, the agitator shaft can be inserted into the interior and the blade clusters can be welded to the respective collars 76 without much concern about the effect of the heat from the subsequent welding operations, because the collars provide significant heat dissipating capacity that significantly diminishes the risk posed by the need to weld the blade clusters 42a, 42b, 42c to the agitator shaft 40. The roof 24 is actually welded in place before the blade clusters 42a, 42b, 42c are welded to the agitator shaft 40, an assembly operation that can be completed following delivery to a cheese making facility where the cheese process vat will eventually be used. The blade clusters 42a, 42b, 42c could be placed in the vat body 12 prior to putting on the roof 24 or, as discussed above, they can be inserted through the roof opening 37 that exists in the roof 24. In either case, the blade clusters 42a, 42b, 42c are preferably welded to the agitator shaft 40 after the roof 24 is welded to the vat body 12.

Now referring also to FIG. 1A, during the cheese making process, rennet is diluted in a container 30 with water or another aqueous fluid prior to pumping the rennet solution (not shown) to the interior 28 of the vat body 12 via a fluid line 32 connecting the container 30 to a injection nozzle assembly 60 via a pump "p", so that fluid passing through the injection nozzle assembly 60 into the interior 28 of the vat body 12 can do so under pressure as required in order to inject a stream of fluid 63 into fluid milk (not shown) in the interior 28 via a plurality of fluid transfer assemblies 60 interconnected with a plurality of fluid transfer port 70. Optionally, additives such as a food coloring agent, calcium, starter cultures and the like can also be pumped from the mixing container 30 through the fluid transfer line 32 to the respective injection nozzle assemblies 60 and the plurality of fluid transfer port 70.

The mixtures of rennet and water or any other aqueous fluid, or calcium, coloring agents or other similar additives, with aqueous fluids, are either prepared in the mixing container 30 or are pre-mixed and then added to the mixing container 30. In preferred embodiments, the mixture or solution is added to fluid milk (not shown) in the interior 28 under pressure created by the pump "p". Although any of the aforementioned constituents can be mixed with the fluid milk in this way, the most critical is the rennet solution because of the preference for quickly mixing the rennet solution fully in the fluid milk as a means for obtaining an even distribution of the rennet within the entire volume of fluid milk in the vat body 12 during cheese making activities. In normal practice, the rennet solution is drawn into an interconnecting line 32a by a pump "P" that directs the rennet solution through a fluid transfer line 32b and into injection nozzle assemblies 60 (see also FIGS. 4-5) via an injection nozzle tube 64. The injection nozzle assemblies 60 (see also FIGS. 4-5) inject the rennet solution into the vat body 12 and will be discussed in more detail below.

Figure 2:
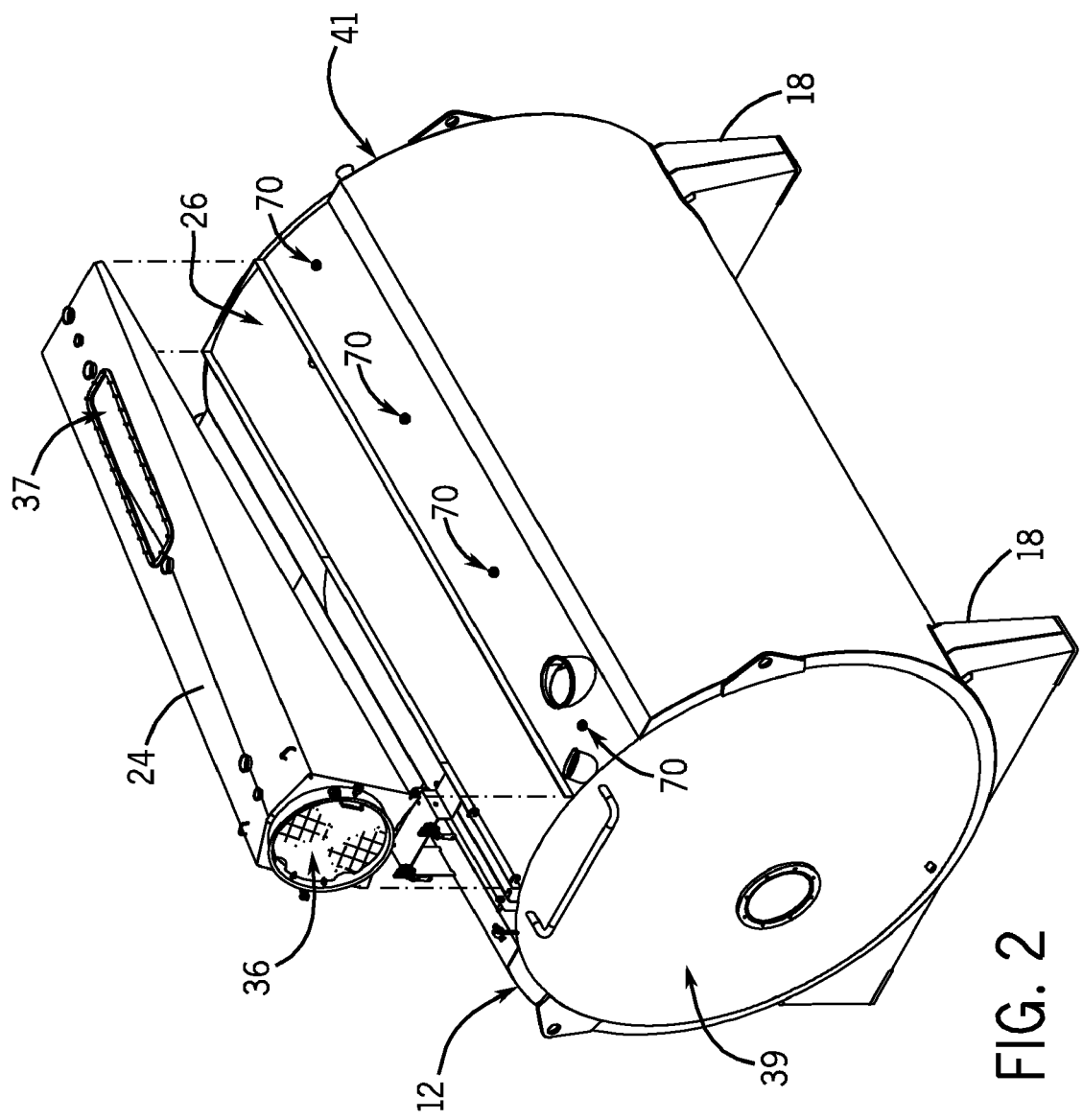
FIG. 2 is an elevated, exploded perspective view of the vat body of the cheese process vat of FIG. 1, showing the vat body of the cheese process vat from an elevated position on the side of the vat body opposite the side shown in FIG. 1.

FIGS. 3 and 6A-9 show an agitator shaft assembly 14 of the present invention that may be used in conjunction with a vat body such as that of FIGS. 1 and 2. The agitator shaft assembly 14 includes a hollow, generally horizontal agitator shaft 40 and agitator panels or blade clusters 42a, 42b, 42c interconnected to the agitator shaft 40 with disk-like collars 76. In preferred embodiments, each of the agitator panels 42a, 42b, 42c include at least one relatively thick, radially positioned primary blade 44 attached to the disk-like collar 76, relatively thinner secondary blades 46 (see FIGS. 6A-7) attached to the primary blades 44 (see FIGS. 6A-7) so that they are positioned generally parallel to the axis or centerline 49 of the agitator shaft 40 and a set of relatively thin, radially positioned or arrayed tertiary blades 48 (see FIGS. 6A-7) attached to the secondary blades 46. It will be appreciated that the teachings of the present invention are not limited to a specific number or arrangement of blades and that each of the respective blade clusters or agitator panels may have either more of or fewer of any of the respective primary, secondary or tertiary blades.

The agitator panels 42a, 42b, 42c of the present invention will preferably further include large paddles 50 and small paddles 52. The small paddles 52 and the large paddles 50 extend from the agitator panels 42a, 42b, 42c at an angle "a" (see also FIG. 9), which will be from about 2 to about 25 degrees, preferably from about 5 to about 20 degrees, more preferably from about 10 to about 17.5 degrees, most preferably about 15 degrees to aid in circulating the contents of the vat body 12 during cheese making.

Figure 6A:
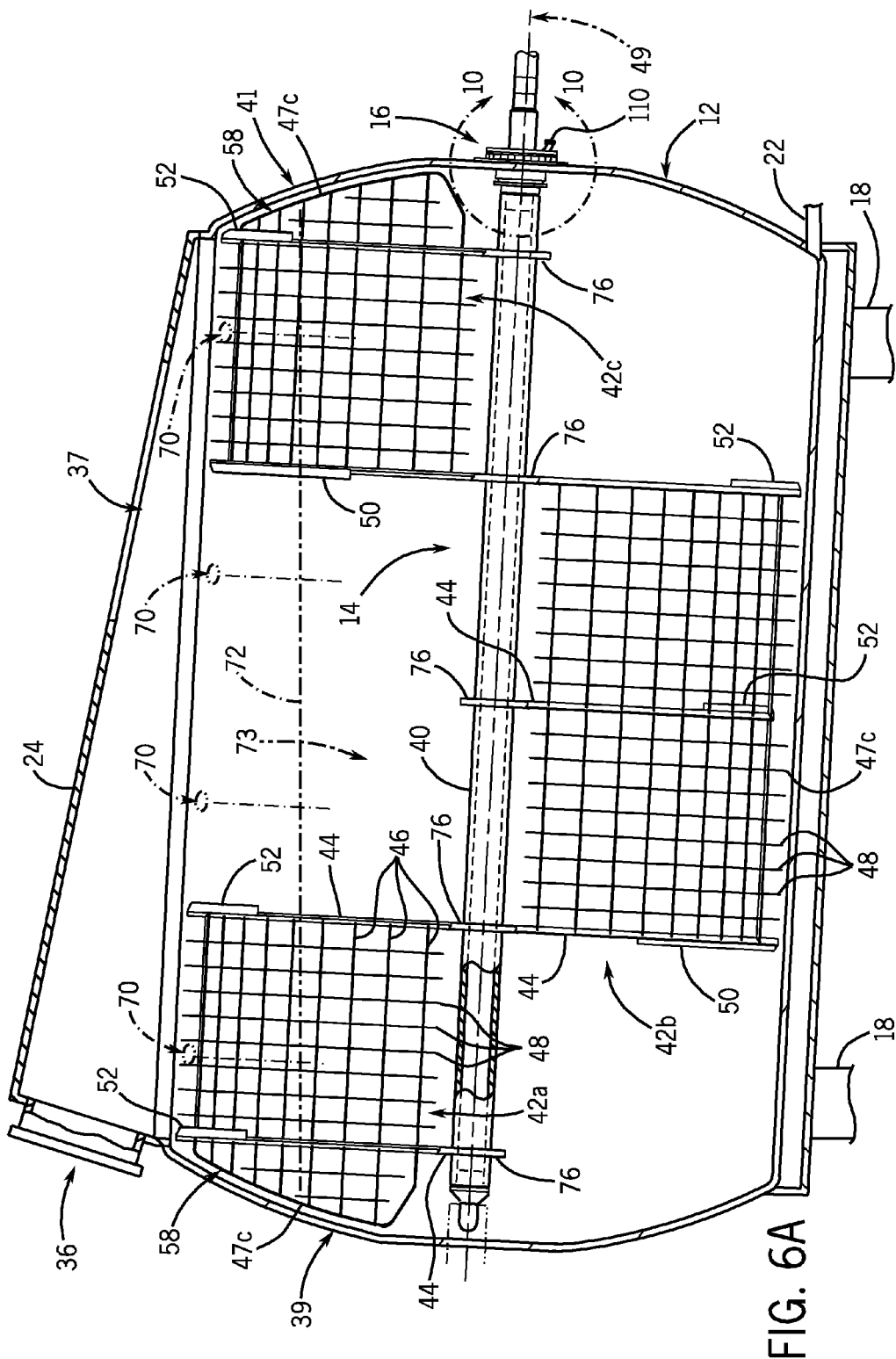
FIG. 6A is a partially broken away, partial cross-sectional, schematic side view of the vat body and the agitator shaft assembly of the cheese process vat of FIG. 4 showing the preferred agitator panels in a vertical alignment.
Figure 6B:
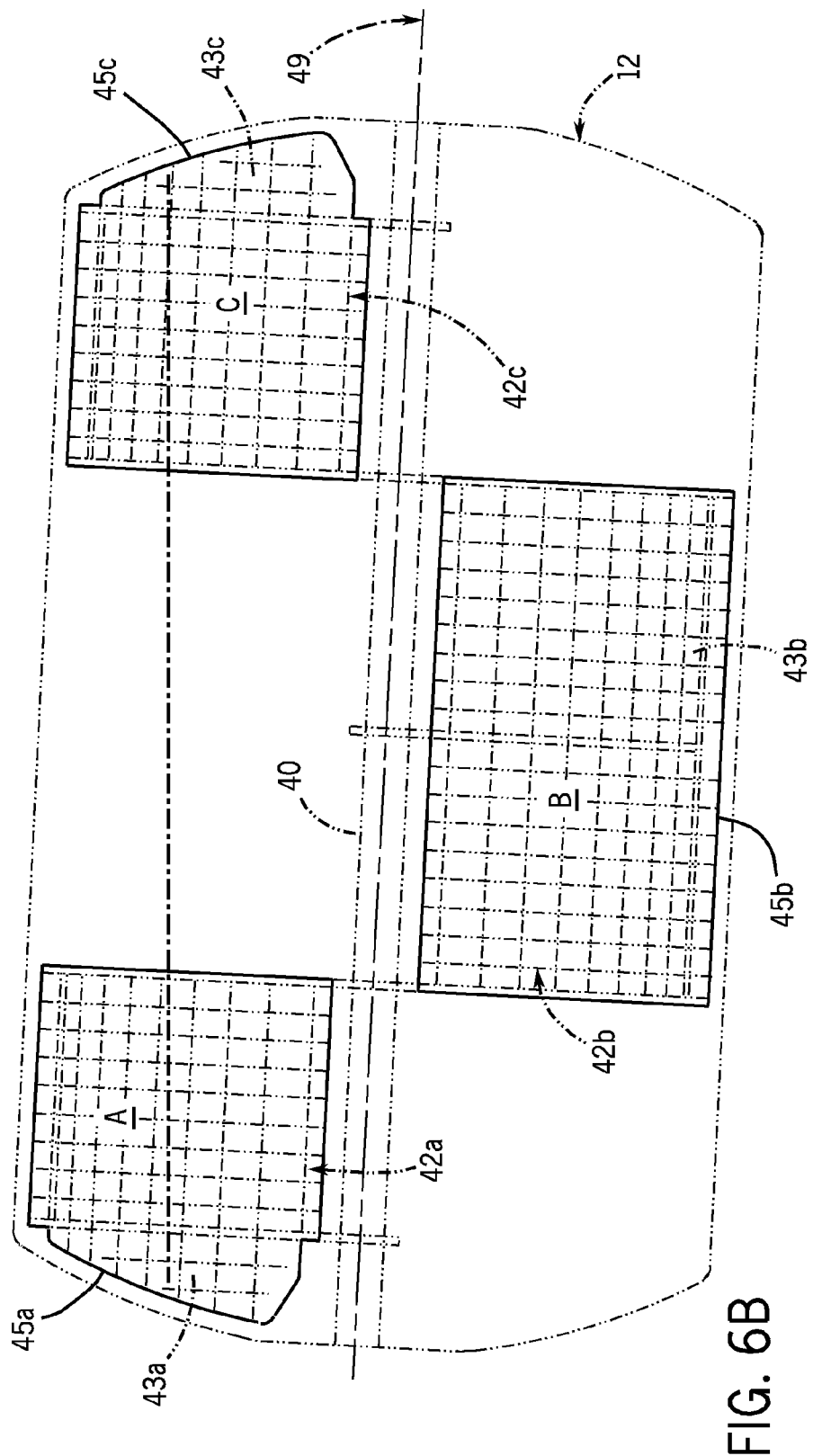
FIG. 6B is a partial schematic view of the agitator shaft and the agitator panels shown in FIG. 6A, but illustrating respective surface areas A, B and C of respective planes passing through respective agitator panels 42a, 42b and 42c and ending at the distal edges of each of the respective agitator panels.

FIG. 6B illustrates respective surface areas A, B and C of respective planes 43a, 43b, 43c passing through respective agitator panels 42a, 42b, 42c and ending at the distal edges 45a, 45b, 45c of each of the respective agitator panels 42a, 42b, 42c. As discussed further below, the surface areas A and C of respective planes 43a, 43c passing through the first and third agitator panels 42a, 42c, respectively, when combined together, is preferably substantially the same as a surface area C of a plane 43b passing through agitator panel 42b and ending at distal edges 45b of the second agitator panel 42b. It is preferably that the agitator shaft assembly of the present invention is substantially balanced with respect to the centerline 49 of the shaft in regard to surface area of respective planes passing through the respective agitator panels on one side of the shaft and the surface area of respective planes passing through the respective agitator panels on the other side of the shaft. It is also preferably that the agitator shaft assembly of the present invention is substantially balanced with respect to the centerline 49 of the shaft in regard to weight of respective agitator panels on one side of the shaft and the weight of respective agitator panels on the other side of the shaft.

In preferred embodiments of the present invention, the weight of the second panel 42b is substantially the same as the total weight of the two end panels 42a, 42c on respective ends 47a, 47c of the agitator shaft assembly 14. In the preferred embodiments, the agitator panel 42b, located in the middle of the agitator shaft 40, is positioned on the opposite side of the agitator shaft 40 from the two end panels 42a, 42b, thus rendering the agitator shaft assembly substantially balanced both in respect to weight of the opposing agitator panels and surface area of the planes passing through the respective opposing agitator panels and ending at distal edges thereof. It will be appreciated that, in alternate embodiments of the present invention, the agitator shaft assembly may include any number of agitator panels, but that it will be preferred to keep the agitator panels generally within a single plane extending through the centerline 49 of the agitator shaft and to keep balanced both the weight of opposing agitator panels and/or the surface area of planes passing through the respective opposing agitator panels and ending at distal edges thereof.

It will be appreciated that the agitator panels 42a, 42b, 42c stir and move the fluid milk, coagulum or whey/curd slurry (not shown) within the vat body 12 as the agitator shaft assembly 14 rotates. The primary, secondary and tertiary blades 44, 46, 48, respectively, each have one sharpened edge 54 and an opposite, unsharpened edge 56. Cutting of the coagulum occurs when the agitator shaft 40 is rotated in a direction where the sharpened edges are leading. Stirring occurs when the agitator shaft assembly 14 is rotated in the opposite direction, when the unsharpened edges are leading.

When the agitator shaft assembly 14 illustrated in FIGS. 3 and 6A-9 rotates counterclockwise into a coagulum or "set", only about one-half of the coagulum (not shown) is penetrated by about one-half of the total agitator panel surface area, either the half associated with surface areas A and C or the half associated with surface area B. When that one-half of the total agitator panel area comes out of the coagulum, during its upward rotation, the other half of the coagulum is being penetrated by the other half of the total agitator panel surface area in its downward rotation. Because the total agitator panel surface area is divided generally in half between the opposing sides of the agitator shaft assembly, this action is less likely to cause the entire mass of coagulum to rotate with the agitator panels, as compared to known cheese process vats where these panels are not opposing panels, as they are in the present invention, but rather grouped panels gathered in a particular radial segment of the radially plane perpendicularly bisecting the agitator shaft. With the present invention, increasing the agitator shaft assembly speed is not necessary either for mixing, cutting or stirring as it has been seen to necessary when a larger percentage of the entire coagulum is moved by a grouped array of agitator panels that are unevenly balanced with respect to the agitator shaft.

In the cooking and stirring operations, since the agitator shaft assembly is balanced, only one half of the curd collection is potentially lifted by half of the total agitator panel surface area. Due to a phenomenon related to the angle of repose, some of the curds fall off the panel toward an area not populated with an agitator panel. As the agitator shaft rotation continues, the here-to-fore downward rotating agitator panels are now upward rotating and again, the curds, due to the angle of repose fall off the agitator panel toward an area not populated with an agitator panel. Throughout the stirring and cooking operations, this end to end movement enhances stirring, which is essential to heat transfer between the curds and whey, which are heated by the hot steam or hot water in the vat liner. An effective agitation will yield higher quality curds with a reduced risk of acid spots in the finished product.

The most preferred agitator shaft assembly 14 of the present invention has multiple blade clusters 42a, 42b, 42c that are positioned to provide a substantially balanced agitator shaft assembly. As shown in FIGS. 3 and 6A-9, the agitator panels 42a, 42b, 42c are balanced by having a single agitator panel 42a, 42c on each end 47a, 47c of the agitator shaft 40 extending in the same radial direction as a larger agitator panel 42b extending from the middle of the agitator shaft 40 on the opposite side of the agitator shaft 40, extending at approximately 180 degrees from the outer agitator panels 42a, 42c. It will be appreciated that the previous arrangement is a preferred arrangement and that any configuration of the agitator panels wherein the agitator panels are balanced around the agitator shaft may be utilized in alternate embodiments. Further, it is highly preferable to include outer agitator panels 42a, 42c having extensions 58 that are shaped to correspond to the curvature of the ends of the vat body 12. The preferred extensions 58 are a portion of the respective outer agitator panels 42a, 42c, and the respective ends 39, 41 of the vat body 12 by only about an inch, preferably about a half an inch, leaving little room for cheese curd or chunks of coagulum to flow around the edges 47a, 47c of the outer agitator panels 42a, 42c as they sweep along the interior 28 of the vat body 12 proximate the respective ends 39, 41 of the vat 10. The agitator panel extensions 58 provide for more efficient and effective cutting and stirring as one rotation of the agitator shaft assembly 14 will sweep the entire contents of the vat body 12, but generally in two halves of the entire contents. The agitator panel extensions 58 include secondary blades 44 and tertiary blades 48 that stem from the outer primary blades 44 of the respective outer agitator panels 42a, 42c of which the respective agitator panel extension 58 is a part.

Referring now also to FIG. 6B, FIG. 6B illustrates respective surface areas A, B and C of respective planes 43a, 43b, 43c passing through of respective agitator panels 42a, 42b and 42c and ending at the distal edges 45a, 45b, 45c of each of the respective agitator panels 42a, 42b, 42c. As previously discussed, it is preferably that the agitator shaft assembly of the present invention is substantially balanced about the shaft both with respect to surface area and weight of the respective opposing agitator panels. TABLE 1 below provides projected weights of respective agitator panels 42a, 42b, 42c (i.e. Panels A, B and C, respectively) for cheese process vats of the present invention having differing lengths and respective vat capacities of from 30,000 to 60,000 lbs. of fluid milk and projected surface areas A, B and C for respective planes 43a, 43b, 43c passing through of respective agitator panels 42a, 42b, 42c and ending at the distal edges 45a, 45b, 45c of each of a series of respective agitator panels 42a, 42b, 42c for such cheese process vats. In each case, the surface areas and the weight of the respective opposing agitator panels are substantially balanced.

Additionally, as previously mentioned, substantially balanced agitator shaft assemblies are highly desirable as the energy required to rotate the agitator shaft assembly is continuous and relatively uniform as opposed to intermittent and pulsing. A continuous and uniform load of this type is more efficient than an intermittent and pulsing load and is less detrimental to electric motors, AC frequency converters, gear reducers, bearings, couplings, seals, welded joints of the agitator shaft assembly components and the like. Minimizing wear on these motors, converters, parts and the like translates into less downtime and lower maintenance costs.

In preferred embodiments of the present invention, the agitator shaft assemblies of the cheese process vats will have substantially balanced weight and/or surface area distributions with respect to the opposing agitator panels of the present invention. In preferred embodiments of the present invention, the weight of the center panel 42b will be from about 40 to about 60% of the weight of the total combined weight of all the panels 42a, 42b, 42c of the agitator shaft assembly, and the surface area B for plane 43b, which passes through of agitator panel 42b and ends at the distal edges 45b of each of center panel 42b, will be from about 40 to about 60% of the total combined surface area (A, B and C combined) for planes 43a, 43b, 43c passing through of respective agitator panels 42a, 42b, 42c and ending at the distal edges 45a, 45b, 45c of each of the respective agitator panels 42a, 42b, 42c of the respective agitator shaft assembly. Similarly, the combined weight of the outer agitator panels 42a, 42c will be from about 40 to about 60% of the weight of the total combined weight of all the agitator panels 42a, 42b, 42c of the agitator shaft assembly, and the combined surface areas (A and C combined) for planes 43a, 43c passing through of respective agitator panels 42a, 42c and ending at the distal edges 45a, 45c of respective agitator panels 42a, 42c will be from about 40 to about 60% of the total combined surface

TABLE 1

Examples of substantially balanced agitator shaft assemblies.

Weight

| Vat Capacity (lbs. of milk) | Panel A (lbs) | Panel B (lbs) | Panel C (lbs) | Panels A + C (lbs) | TOTAL (lbs) | Panels A + C (% of total) | Panel B (% of total) | Variance |
|---|---|---|---|---|---|---|---|---|
| 30,000 | 80.976 | 106.133 | 79.176 | 160.152 | 266.285 | 60.14% | 39.86% | 20.29% |
| 35,000 | 83.806 | 111.793 | 82.006 | 165.812 | 277.605 | 59.73% | 40.27% | 19.46% |
| 40,000 | 86.636 | 117.453 | 84.836 | 171.472 | 288.925 | 59.35% | 40.65% | 18.70% |
| 45,000 | 89.466 | 123.113 | 87.666 | 177.132 | 300.245 | 59.00% | 41.00% | 17.99% |
| 50,000 | 92.296 | 128.773 | 90.496 | 182.792 | 311.565 | 58.67% | 41.33% | 17.34% |
| 55,000 | 95.126 | 134.433 | 93.326 | 188.452 | 322.885 | 58.37% | 41.63% | 16.73% |
| 60,000 | 97.956 | 140.093 | 96.156 | 194.112 | 334.205 | 58.08% | 41.92% | 16.16% |

Area

| Vat Capacity (lbs. of milk) | Panel A (in.$^2$) | Panel B (in.$^2$) | Panel C (in.$^2$) | Panels A + C (in.$^2$) | TOTAL (in.$^2$) | Panels A + C (% of total) | Panel B (% of total) | Variance |
|---|---|---|---|---|---|---|---|---|
| 30,000 | 1521.371 | 2324.271 | 1521.371 | 3042.742 | 5367.013 | 56.69% | 43.31% | 13.39% |
| 35,000 | 1708.634 | 2698.798 | 1708.634 | 3417.268 | 6116.066 | 55.87% | 44.13% | 11.75% |
| 40,000 | 1895.898 | 3073.325 | 1895.898 | 3791.796 | 6865.121 | 55.23% | 44.77% | 10.47% |
| 45,000 | 2083.161 | 3447.85 | 2083.161 | 4166.322 | 7614.172 | 54.72% | 45.28% | 9.44% |
| 50,000 | 2270.425 | 3822.379 | 2270.425 | 4540.85 | 8363.229 | 54.30% | 45.70% | 8.59% |
| 55,000 | 2457.688 | 4196.906 | 2457.688 | 4915.376 | 9112.282 | 53.94% | 46.06% | 7.88% |
| 60,000 | 2644.952 | 4571.433 | 2644.952 | 5289.904 | 9861.337 | 53.64% | 46.36% | 7.29% | areas (A, B and C combined) for respective planes 43a, 43b, 43c passing through respective agitator panels 42a, 42b, 42c and ending at the distal edges 45a, 45b, 45c of each of the series of respective agitator panels 42a, 42b, 42c of the agitator shaft assembly.

The present invention preferably includes disk-like collars 76 that are welded to the agitator shaft 40 while the agitator shaft is external to the vat body 12. If necessary, the agitator shaft can be straightened at that time with known methods and techniques. After installation of the straightened agitator shaft 40 to the respective ends 39, 41 of the vat body 12, the blade clusters 42a, 42b, 42c are welded to the outer edge 78 of the disk-like collars 76. Welding the blade clusters 42a, 42b, 42c to the outer edge 78 of the disk-like collars 76 virtually eliminates any agitator shaft 40 distortion caused by the heat generated during the welding process. In addition, the disk-like collar 76 is gentler on the coagulum when the agitator shaft assembly 14 rotates because there are no blunt edges are being forced through the coagulum (not shown). By reducing disturbance of the coagulum, the product yield is increased.

Figure 3:
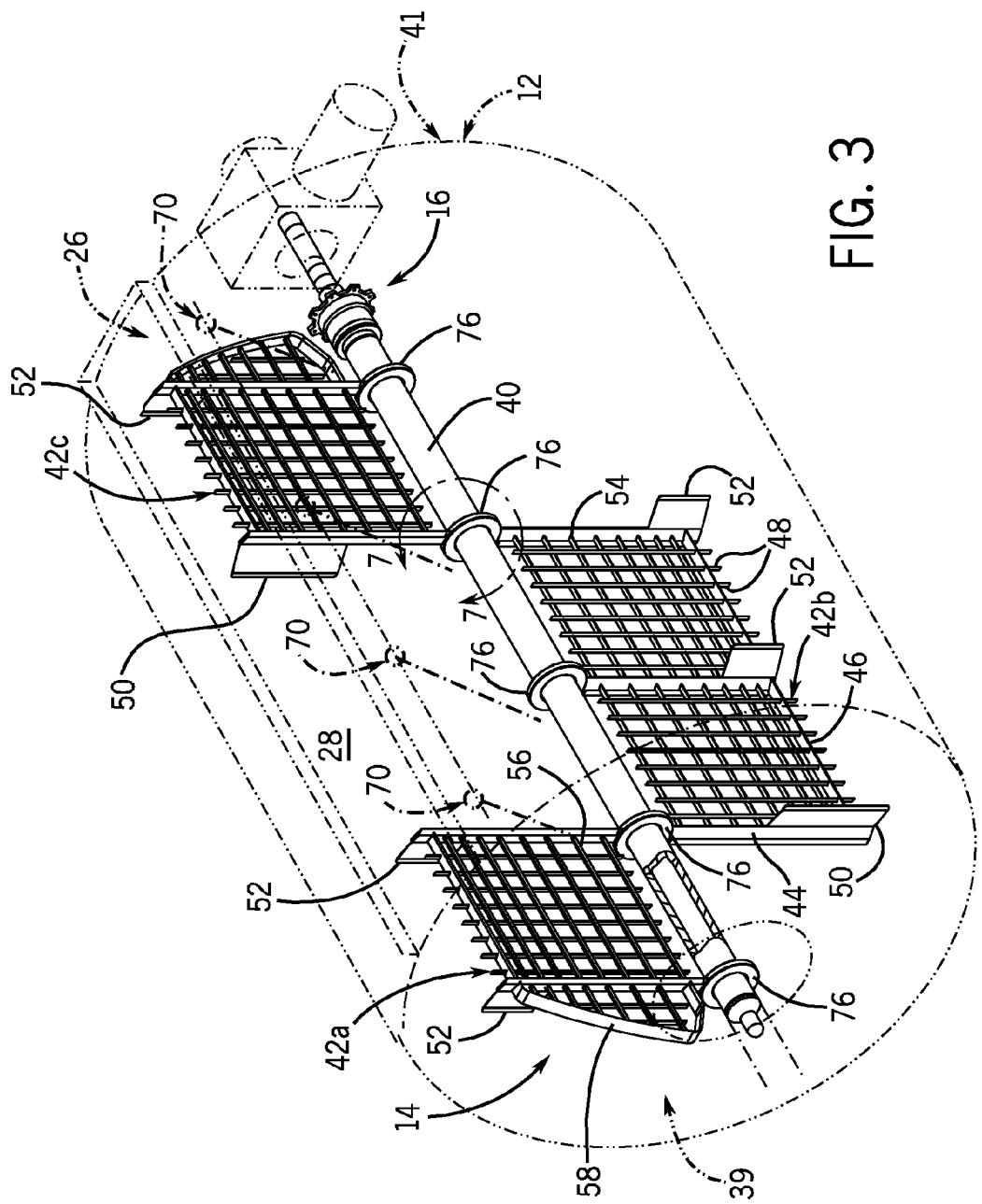
FIG. 3 is an elevated perspective view of the vat body of the cheese process vat shown in phantom from the perspective of FIG. 2, but illustrating the preferred agitator shaft assembly (not all parts of the vat body are shown for better clarity)
Figure 4:
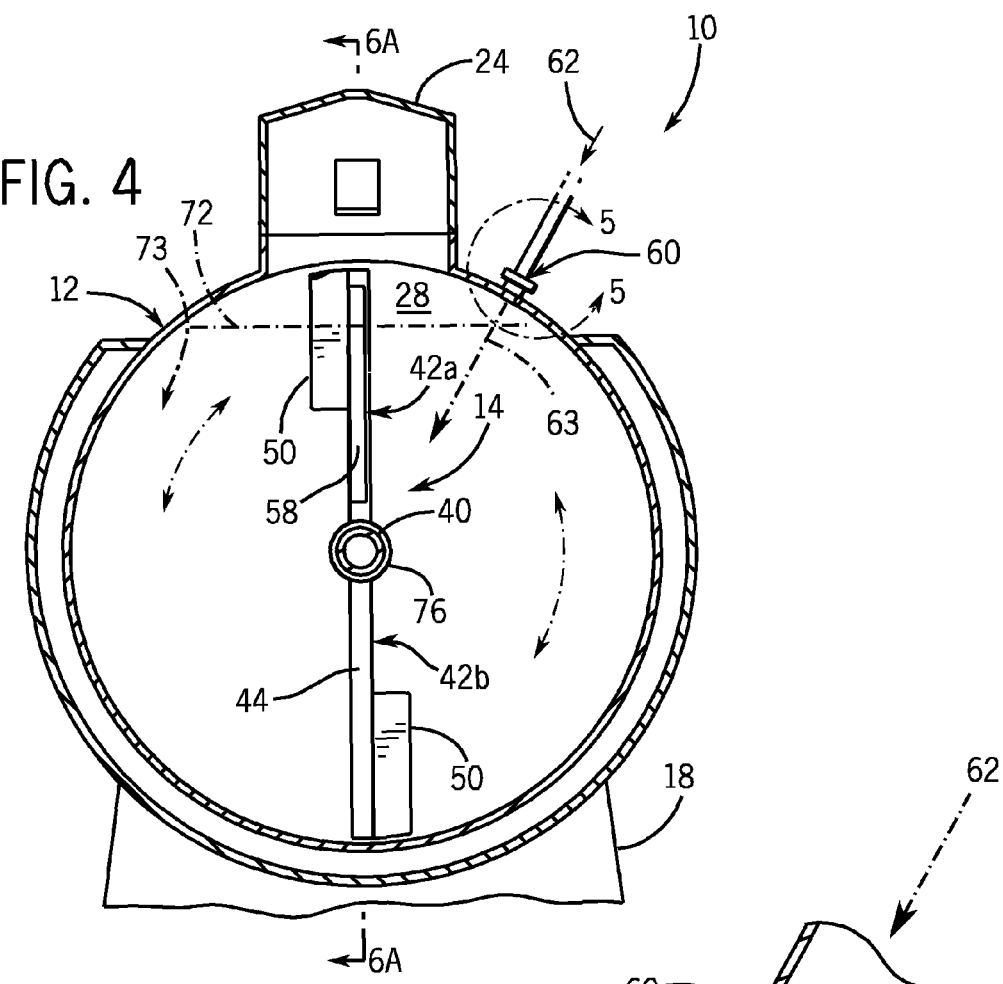
FIG. 4 is a cross-sectional view of the cheese process vat as seen from the line 4-4 of FIG. 1, but depicting the planar alignment of the agitator panels and position of a representative rennet injector assembly.
Figure 5:
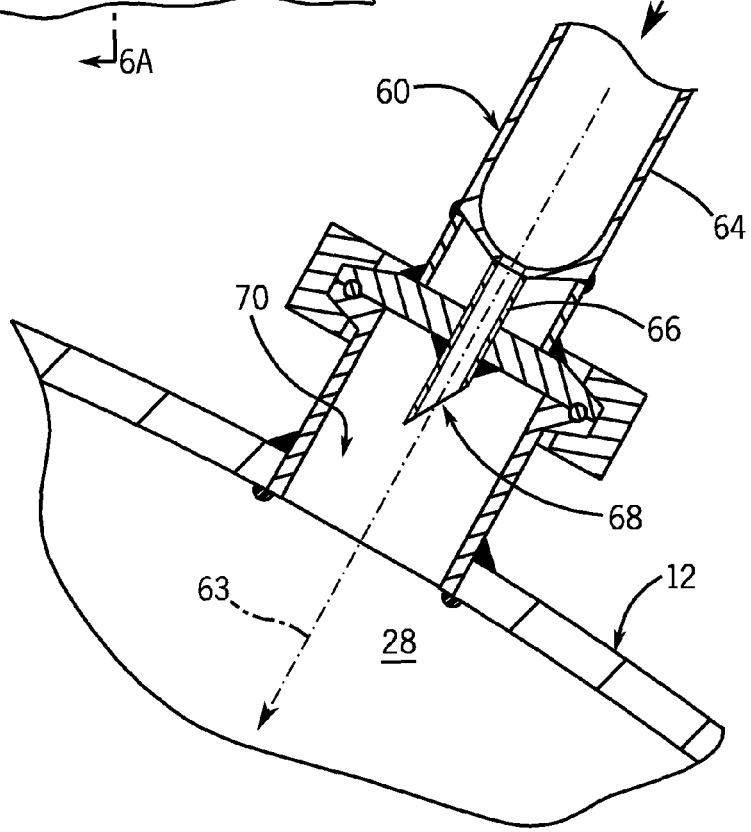
FIG. 5 is an enlarged, cross-sectional, side view of the rennet injector assembly illustrated in the area partially circumscribed by the line 5-5 of FIG. 4.

As shown in FIGS. 2-6A, the cheese process vat 10 of FIGS. 1-3 preferably includes one or more injection nozzle assembly 60 interconnected to the vat body 12 at fluid transfer ports 70, preferably at least one injection nozzle assembly for every 44" of running vat body length, but where the injection nozzle assemblies 60 are not less than 2" apart, to inject a rennet solution 62 or other additive solution (i.e. aqueous calcium, coloring agent or the like) into the fluid milk 73 (see in phantom in FIG. 6A) located in the interior 28 of the vat body 12. The objective in determining the number and spacing of the injection nozzle assemblies 60 is to get an even distribution of rennet solution without injecting the rennet solution too quickly. The injection nozzle assembly 60 (see FIG. 5) includes a supply tube 64, which communicates with the fluid transfer line 32, and an injection nozzle 66 having a nozzle opening 68. Rennet is optionally diluted in water or another aqueous medium in a mixing container 30 (see FIG. 11A). Then the resulting rennet solution is preferably pumped by a pump "p" (see FIG. 1) or otherwise drawn into a fluid transfer line 32 from the mixing container. In preferred embodiments, the pump "p" will be a centrifugal pump, a positive displacement pump or the like, most preferably a centrifugal pump. Alternately, it will be appreciated that the mixed additive solution (i.e. the rennet solution) can be pre-mixed and then poured or otherwise delivered into the mixing container 30. The fluid transfer line 32 communicates with a supply tube 64 that is part of each of the respective injection nozzle assemblies 60. From the respective supply tubes 64, the additive solution 62 flows through the injection nozzle 66 and out the nozzle opening 68. The narrowing in the injection nozzle 66 or at the nozzle opening 68 adjacent to the supply tube 64, is believed to create a "venturi" effect on the additive solution 62, so that the solution is passed out of the nozzle opening 68 in a fluid stream 63 at a higher speed than the speed at which the solution 62 travels through the fluid transfer line 32 or the tube 64.

When rennet solution then enters the vat body 12 as a fluid stream 63 after passing through the injection nozzle 66 and the fluid transfer port 70, the fluid stream 63 penetrates the surface 72 of the fluid milk 73. In preferred embodiments of the invention, by injecting the rennet solution in a fluid stream 63 through the surface 72 down into the fluid milk 73 at multiple locations in the interior 28 of vat body 12, rather than 1) pouring, which puts too much of the rennet solution in one place at one time or 2) spraying with a spray nozzle, which only distributes the solution onto the surface of the milk, as often done by others, the rennet solution is diluted and distributed into the fluid milk more evenly and more rapidly, which results in a better overall mixing and distribution that reduces set time and contributes to a better, more even and complete, set and resulting coagulum. The is believed to be a very significant factor in contributing to the significant improvements in the yields that the inventors have been able to obtain from cheese making operations utilizing the present cheese process vats.

The injection nozzle assemblies are located above the surface 72 of the fluid milk 73 to provide for a way of injecting the rennet solution through and below the surface of the fluid milk 73, while still meeting current regulatory sanitation standards. Preferably, a rennet fluid stream 63 generated from an injection nozzle assembly 60 is injected into the surface 72 of the fluid milk 73 at a speed greater than about 40 ft/s, more preferably greater than about 60 ft/s, most preferably greater than about 80 ft/s, and the fluid stream 63 of rennet solution preferably will have a diameter no greater than about 0.25 (¼) inches at the nozzle opening 68 and a width no greater than about two (2.0) inches in diameter at the surface 72 of the fluid milk 73 and will penetrate the surface 72 of the fluid milk 73 to an immediate depth of equal to or more than about six (6.0) inches. It will be appreciated that the fluid stream 63 will enter the surface of the fluid milk preferably in a limited area having a generally circular shape, but can alternatively have a generally oval shape or another alternate shape having irregular boundaries. Typically, in the art, the water to rennet concentration of the rennet solution is from about 15:1 to about 20:1, although this dilution ratio is easily modifiable to suit any manufacturer's preference or the particular activity level of any particular rennet preparation (i.e. single, double or triple strength rennet preparations or the like).

Figure 7:
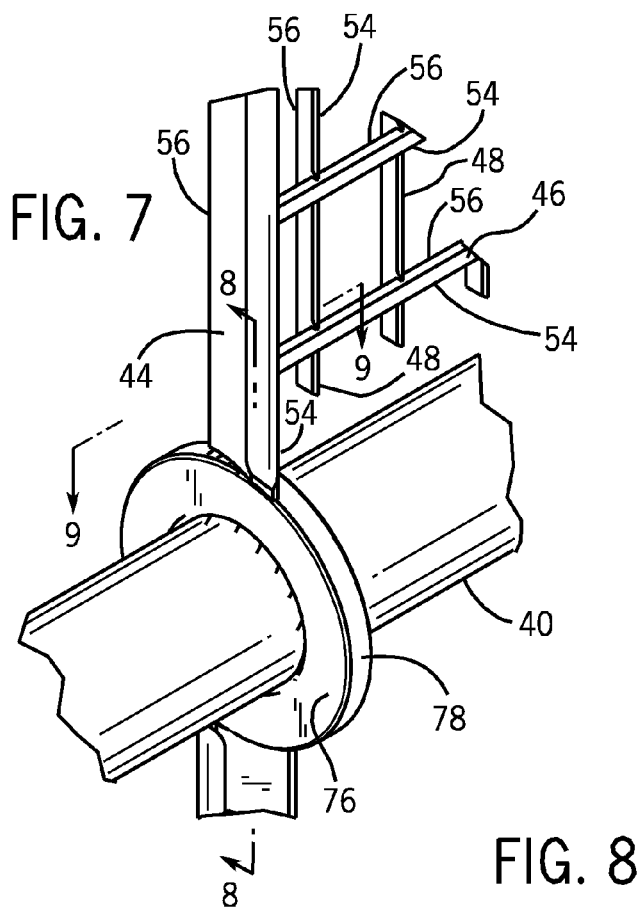
FIG. 7 is an enlarged partial, perspective view of a collar 76 interconnecting an agitator panel to an agitator shaft of the agitator shaft assembly shown in the area partially circumscribed by line 7-7 of FIG. 3.
Figure 8:
FIG. 8 is an enlarged partial cross-sectional, orthographic side view of the collar interconnecting an agitator panel to the agitator shaft as seen from line 8-8 in FIG. 7.
Figure 9:
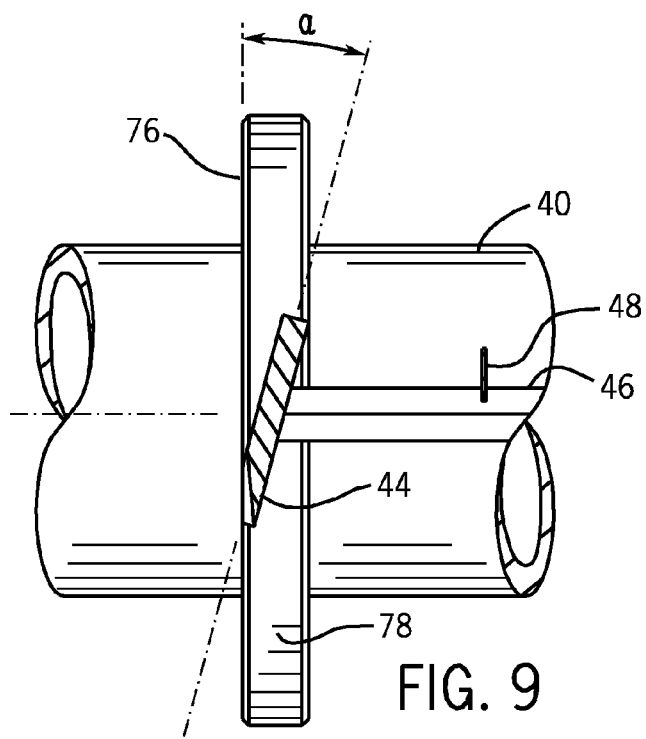
FIG. 9 is an enlarged partial, orthographic top view of the collar interconnecting an agitator panel to the agitator shaft as seen from line 9-9 in FIG. 7.

FIGS. 7-9 show the preferred disk-like collar 72 in accordance with the cheese process vat of the present invention. The disk-like collar 72 has an outer edge 78 and interconnects an agitator panel 42a, 42b, 42c to an agitator shaft 40 of the present invention. After installation of the straightened agitator shaft 40 into the vat body 12, the agitator panels 42a, 42b, 42c are welded to the outer edge 78 of the disk-like collars 76. Welding to the outer diameter or edge 78 of the disk-like collars 76 virtually eliminates any agitator shaft distortion caused by heat generated during the welding process.

Referring now also to FIGS. 6A-6B and 10-15, it will be appreciated that as long as the agitator shaft assembly 14 in a cheese process vat such as the present vat resides below the surface of the potential fluid content operating level, a seal or a system providing seals will be necessary. Since a cheese process vat is subject to regulatory scrutiny, the seal or seal system will have to be sanitary and cleanable to certain regulatory standards; and also provide a leak detection port.

The preferred agitator shaft assembly 14 of the present invention is illustrated in FIGS. 6A-6B and 10-15. The agitator shaft 40 is a cylindrical agitator drive shaft that is preferably a hollow core, stainless steel agitator drive shaft. The agitator shaft 40 includes concentric flange 83 having an inner face 87. In preferred embodiments, the inner face 87 is located on the surface of an inner face wear plate 86 that is welded onto an inner face support member 84. The inner face wear plate 86 is preferably made of a hardenable stainless steel that wears especially well and also provides a smooth surface against which an elastomeric seal will slide especially easily, without creating undue wear to either the surface of the inner face 87 on the wear plate 86 or to the seal lip 90.

The preferred shaft seal assembly 16, 80 of the present invention is illustrated in FIGS. 6A-6B and 10-15. It is an adjustable seal assembly 80 including a face seal 88 having a face seal body 89 and a face seal lip 90 that extends away from the face seal body 89. The face seal lip 90 is pre-loaded in an adjustable seal assembly subunit 82, so there will be a pre-loaded pressure or bias between the face seal lip 90 and the inner face 87 of the agitator shaft 40, such that a tight joint is formed in between the face seal lip 90 and the inner face wear plate 86. The seal assembly subunit 82 preferably includes the face seal 88, an inner seal holder 92, a shaft seal 111, an outer seal holder 126 and a seal retaining plate 128 screwed to the outer seal holder 126 by screws 117. The face seal 88 is engaged with a first end 93a of the inner seal holder 92 and the outer seal holder 126 and the shaft seal 111 is engaged with a second end 93b of the inner seal holder 92. The seal assembly subunit 82 is assembled by placing the face seal body 89 in a first groove 94 in the first end 93a of the inner seal holder 92 and the outer seal holder 126 is slipped over the inner seal holder 92 and the face seal 88. The seal assembly subunit 82 also includes the shaft seal 111 that is placed in a second groove 95 in the second end 93b of the inner seal holder 92. The inner seal holder 92 and the outer seal holder 126 cooperate to define a "dovetail" groove 102 that holds the face seal body 89 in place within the seal assembly subunit 82. The dovetail groove 102 is truncated so that the space diminishes between opposing sides of the dovetail groove 102 that grip the face seal body 89 as the face seal body 89 extends toward the face seal lip 90. The seal assembly subunit 82 also includes the seal retaining plate 128. The seal retaining plate 128 holds the other parts of the seal assembly subunit 82 together. In preferred embodiments, the extension 124 is an inner mounting flange ring 124 that is preferably secured to an outer mounting flange ring 114, which is preferably welded to the vat body 12.

The vat body 12 preferably includes the outer mounting flange ring 114 that is welded to the vat body 12 and the inner mounting flange ring 124 that is fastened by a plurality of outer screws 116 that cooperate to secure the inner mounting flange ring 124 to the outer mounting flange ring 114. The seal assembly subunit 82 is fastened to the inner mounting flange ring 124 preferably by a plurality of nuts 119 and studs 118 that cooperate to secure the seal assembly subunit 82 to the inner mounting flange ring 124 when the plurality of studs 118 are screwed into reciprocally threaded stud receiving openings in the inner mounting flange ring 124 and the nuts 119 are then threaded on to reciprocally threaded ends of the studs 118' to hold the subunit 82 in place on the second end 41 of the vat body 12. It will be appreciated that the respective studs 118 and nuts 119 work together to fasten the respective parts of the cheese process vat 10 together, and that the respective screws 116, 117 similarly fastens such parts together, but that any number of other fasteners such as bolts (not shown), screws (not shown), a combination of standoffs and nuts, a diverse combination of such fasteners and the like may be used in the place of the combination of the respective studs 118 and nuts 119 or screws 116, 117 to fasten the respective parts of the cheese process vat 10 together in alternate embodiments and that the present invention broadly encompasses the use of any suitable fasteners that can be employed to secure the respective parts of the present cheese process vat together.

The preferred cheese process vat 10 of the present invention includes a pair of o-rings 127, 129 preferably made from a sanitary rubber product that will provide an effective seal for joints between the inner and outer mounting flange rings 124, 114 and the inner mounting flange ring 124 and the outer seal holder 126. The first o-ring 127 is seated in between a joint formed between the outer mounting flange ring 114 and the inner mounting flange ring 124 and the second o-ring 129 is seated in between a joint formed between the inner mounting flange ring 124 and the outer seal holder 126. The first and second O-rings 127, 129 create a seal to prevent the contents of the vat body 12 (not shown) from leaking through the respective joints to create unsanitary conditions.

When the seal assembly subunit 82 is in place, the combination of the face seal 88, the inner seal holder 92, the shaft seal 111 and the agitator drive shaft 40 of the cheese process vat 10 define a seal chamber 106 that has an fluid conduit channel 108 that communicates with an external cleaning solution inlet 110 that doubles as the leak detection port 110. A portion of the fluid conduit channel 108 is defined by the inner seal holder 92 (see FIG. 14) and it is extended to interconnect with the cleaning solution inlet/leak detection port 110.

Figure 11A:
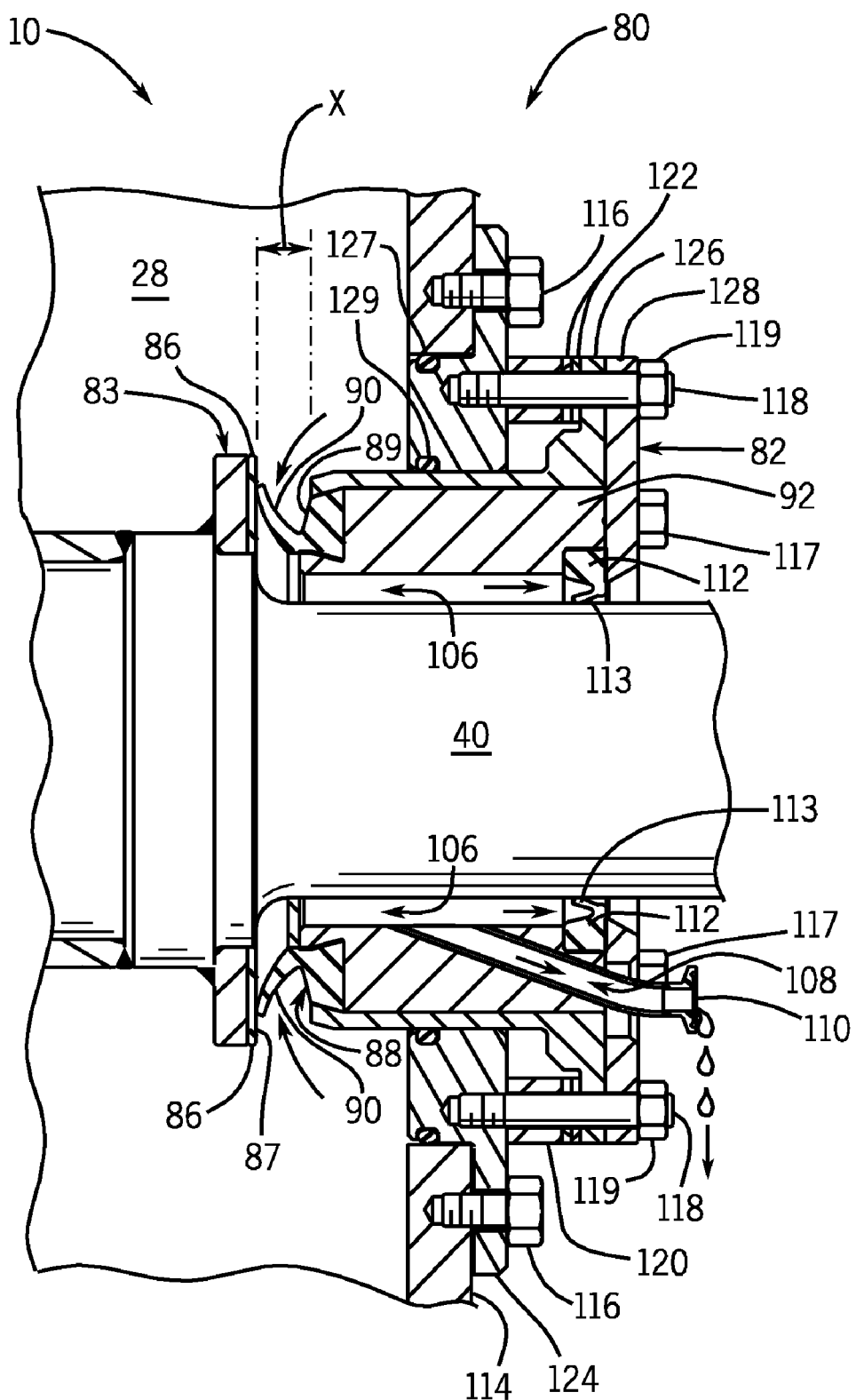
FIG. 11A is an enlarged partial, cross-sectional side view of the shaft seal assembly of FIG. 10, but illustrating the fluid forces applied to the face seal lip by a fluid in the interior of the vat body and showing the flow of such fluid in a circumstance where the face seal fails to prevent fluid from the interior of the vat body from entering the seal chamber 106.
Figure 11B:
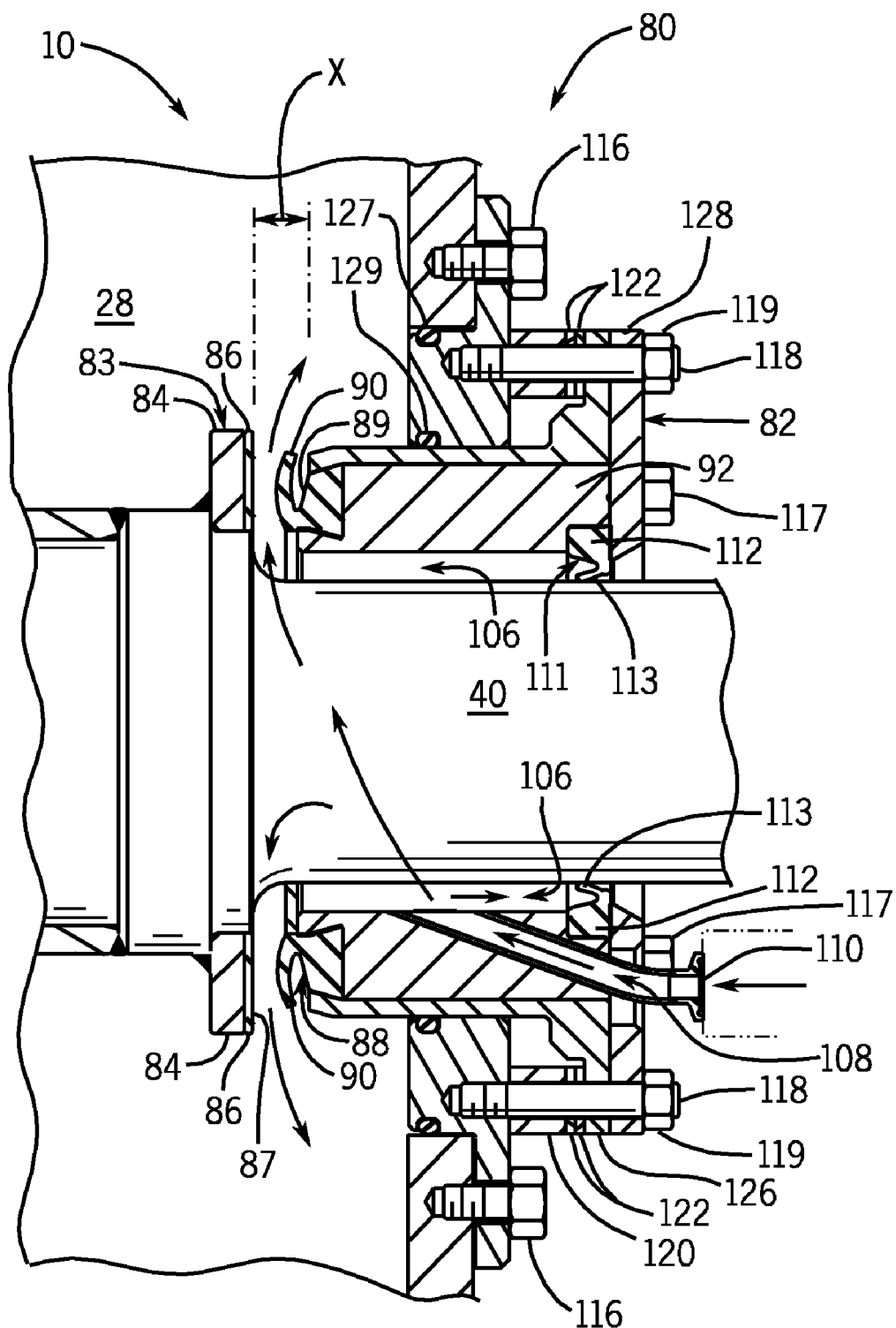
FIG. 11B is an enlarged partial, cross-sectional side view of the shaft seal assembly of FIG. 10, but illustrating the fluid forces applied to the face seal lip and the shaft seal lip by cleaning solution introduced under pressure into the seal chamber 106.

The seal chamber 106 doubles as a CIP chamber 106 to provide a passageway for cleaning/sanitizing solution fluids to pass into the interior 28 of the vat body 12 in a manner indicated by the arrows shown in FIG. 11B. The cleaning/sanitizing solution which enters into the seal chamber 106 from the fluid conduit channel 108 that interconnects the seal chamber 106 to the cleaning solution inlet 110, which will be discussed in detail below. The seal chamber 106 is bordered on one side by a shaft seal 111 having a shaft seal body 112 and a shaft seal lip 113 and on the other side by the face seal 88. The face seal lip 90 and the shaft seal lip 113 are partially concave wing structures designed and configured to cooperate with the respective seal body to which the respective wing structure is attached to act as check valves to prevent fluid from passing thru the joint sealed by a wing structure that faces inward. For example, the face seal lip 90 faces outward against the inner face 87 with respect to fluid traveling in the direction of the face seal lip 90 from the seal chamber 106, but inward with respect to fluid traveling in the direction of the face seal lip 90 from the interior 28 of the vat body 12, so that the face seal lip 90 acts as a check valve to prevent fluid from leaving the interior 28 to enter the seal chamber 106 via any separation between the face seal lip 113 and the inner face 87, because the flow of fluid from the interior 28 toward the facing face seal lip 90, which faces inward toward the interior 28 or with respect to the interior 28, and forces the face seal lip 90 against the inner face 87, thereby biasing the face seal lip 90 even more against the inner face 87 during cheese making operations; and the shaft seal lip 113 faces inward with respect to the seal chamber 106 and therefore prevent fluid from leaving the seal chamber 106 via any separation between the shaft seal lip 113 and the agitator shaft 40, because the flow of fluid toward the inward facing shaft seal lip 113 forces the shaft seal lip 113 against the agitator shaft 40, thereby biasing the shaft seal lip 113 even more against the agitator shaft 40 during clean-in-place operations. Because the respective seals 88, 111 are designed and configured to act as check valves, as discussed above, fluids are expected to pass in only one direction only through joints blocked by the respective seals. The face seal 88 and the shaft seal 111 may be made of any suitable sanitary rubber product that is effective for the intended use. These products/materials include but are not limited to sanitary rubber products that are available in the market, such as VITON (FKM Fluorocarbon Rubber, Vinylidene fluoride-hexafluoropropylene), NITRILE RUBBER (NBR, Acrylonitrile-Butadiene Rubber), HNBR (Hydrogenated Nitrile), SBR (Styrene-Butadiene Rubber), EPDM (Ethylene Propylene Rubber), Chloroprene and the like. The rubber material must be certified to have passed the tests outlined in a document available from 3-A Sanitary Standards, Inc., entitled *3-A Sanitary Standards for Multiple-Use Rubber and Rubber-Like Materials Used as Product Contact Surfaces in Dairy Equipment*, Number 18-03, published and available for purchase on the World Wide Web at http://3-a.org/, August, 1999.

In preferred embodiments, a portion of the seal assembly 16, 80 is preassembled. This preassembled seal assembly subunit 82 preferably includes an inner seal holder 92, a face seal 88, a shaft seal 111, an outer seal holder 126 and a seal retaining plate 128. Once assembled, the preassembled seal assembly subunit 82 can be slid onto the agitator shaft 40, into an opening in the center of the inner flange ring 124 and onto studs 118 having preferably a tubular spacer 120 and shims 112 and then secured with nuts 119.

Turning now with specificity to FIG. 11A, when the interior 28 of the vat body 12 is filled with fluid milk (not shown), the fluid milk applies pressure to the face seal lip 90 that acts as a check valve with respect to fluid flowing from the interior 28 of the vat body 12, unless the face seal 88 fails. The pressure, indicate by the arrows shown in FIG. 11A, forces the face seal lip 90 against the inner face 87 on the inner face wear plate 86, so that the contents of the vat body 12 (not shown) cannot get into the seal chamber 106. The seal assembly 80 of the present invention also aids in detecting leaks of such fluid from the interior 28 into the seal chamber 106, because such leaks, which can only occur if the face seal 88 fails, enable fluid to travel into the seal chamber 106 from where it can flow down through the fluid conduit channel 108 and out of the vat 10 via the cleaning solution inlet/leak detection port 110. While in use, for instance the face seal lip 90 is positioned so that any leakage of milk or whey into the seal chamber 106 from the interior 28, will flow through the seal chamber 106, into the fluid conduit channel 108, and out of the vat 10 via the cleaning solution inlet/leak detection port 110, and onto the floor of the facility (see drops from cleaning solution inlet 110), providing a visual indicator to the operator that maintenance is necessary.

In order to clean the cheese process vat 10 of the present invention, cleaning solutions are pumped into the cheese process vat at various clean-in-place (CIP) ports 34 (See also FIG. 1), which enable the cleaning solution to flow directly into the interior 28 of the vat body 12 from above. The cheese process vat 10 is also equipped with two or more additional spray devices (not shown) that are intended to automatically clean the interior 28 of the vat body 12. Simultaneous, a supply port (not shown) near one end of the agitator shaft 40, proximate an agitator shaft bearing (not shown), can direct further cleaning solution at agitator shaft bearing. An additional supply port, the cleaning solution inlet 110 and channel 108 permit the direction of cleaning solution into the seal chamber 106 to clean parts of the shaft seal assembly 80, which will be further discussed in detail below.

Figures 12, 13:
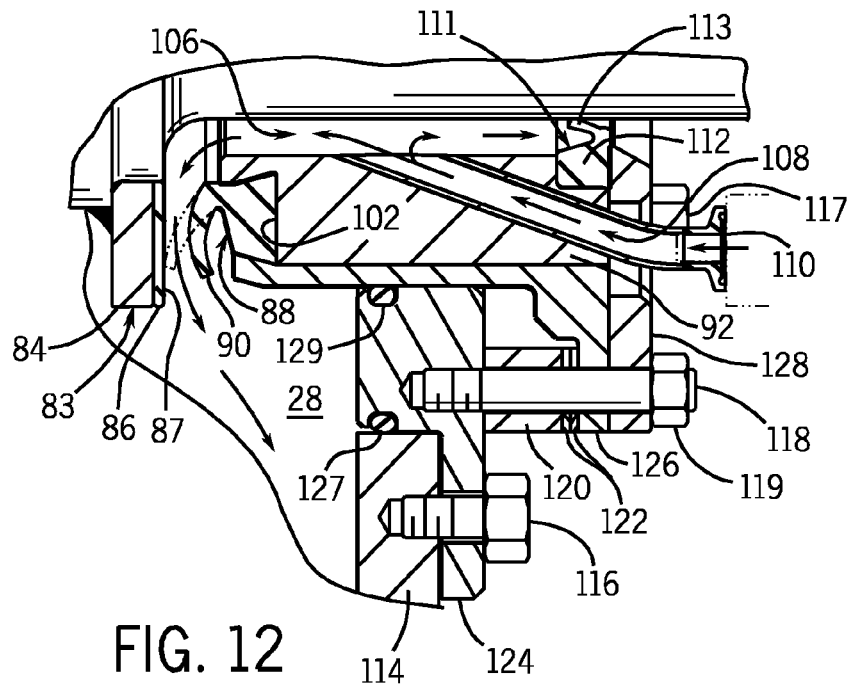
FIG. 12 is an enlarged, partial cross-sectional side view of the fluid forces similar to those shown in FIG. 11B.
FIG. 13 is an enlarged partial, cross-sectional side view of the seal assembly of FIG. 10, but where the shims 122 (see in FIG. 12) have been removed in order to adjust the seal assembly subunit and decrease the distance between inner face of the agitator shaft and the face seal body.

Now referring with further specificity to FIGS. 11B and 12, when the interior 28 of the vat body 12 is being cleaned via the overhead cleaning ports 34, cleaning solution is also pumped into the seal chamber 106 through the cleaning solution inlet 110 and the channel 108. The face seal lip 90 is angled away from the seal chamber 106 and will be forced away from the inner face wear plate 86, if the solution is pumped into the seal chamber 106 under sufficient pressure to force the face seal lip 90 away from the inner face wear plate 86, thus cleaning the seal chamber 106 and the backside of the of the face seal lip 90 and the inner face wear plate 86. The cleaning solution that flows into the seal chamber 106 towards the shaft seal 111 will force the shaft seal lip 113 against the agitator shaft 40, thereby creating a tighter seal and preventing cleaning solution from leaking past the shaft seal 111. The cleaning solution that passes past the face seal lip 90 travels into the interior 28 of the vat body 12 to join with cleaning fluid the flows into the interior 28 of the vat body 12 from the overhead cleaning ports 34. Typically the cleaning solution is disposed of through a drainage port 22 (See FIG. 6A), secured to the vat body 12. The inside diameter of the drain (not shown) is tangent to the lowest surface of the vat 10, and the vat is intentionally canted slightly toward the drainage port so that liquid will not pool inside the vat 10.

In preferred embodiments, both the shaft seal 111 and the face seal 88 are captivated in the seal assembly subunit 82 in such a way that there is a pre-determined amount of pressure on the shaft seal body 112 and the face seal body 89, so that milk, whey or cleaning solution cannot wick into the joint formed between these two elastomeric components and the respective opposing surfaces on the inner seal holder 92, outer seal holder 126 and the seal retaining plate 128, respectively.

The amount of force exerted on the face seal lip 90 may be adjusted without having to enter the interior 28 of the vat body 12. On each stud 118 is a tubular spacer 120. The tubular spacers 120 are machined to a length that will create a pre-determined compression on the face seal lip 90. Preferably, on each stud 118 there will also be at least one C-shaped shim 122. In the present embodiment shown in FIGS. 10-12, there are two C-shaped shims, but it will be appreciated that there could be more, perhaps three, four, five, six or more shims to provide greater flexibility for adjusting the shaft seal assembly 80. To adjust the pressure on the face seal lip 90 when forced against the inner face 87, the user simply loosens the nuts 119 on the studs 118, so that at least one shim 122 can be removed from each of the studs 118 and then the respective nuts 119 can be retightened. The removable shims 122 provide a way to increase pressure on seal lip 90. The shims are preferably C-shaped so they can easily be pulled out from under the outer seal holder 126 so that the nuts 119 may be re-tightened without having to remove the nuts 119 and the seal assembly subunit 82 to remove the shims 122. The number and/or thickness of shims 122 are fully customizable to create numerous tightening increments and possibilities. It will also be appreciate that other types of shims that have either an open side or not may be used in alternate embodiments of the present invention without departing from the scope of the present invention.

Now also referring with specificity to FIG. 13, which illustrates a reoriented adjustable shaft seal assembly 80' of the present invention in which the seal assembly subunit 82' has been adjusted following the removal of the shims 122, shown in the prior Figures, and the seal assembly subunit 82' is positioned closer to the flange 83 to increase the compression of the face seal lip 90. As compared to the seal assembly subunit 82, shown in FIGS. 10 and 11A-B, the seal assembly subunit 82 of FIG. 13 has been adjusted by the removal of two shims 122 on each stud 118. Once the shims 122 have been removed, the nuts 119, can be loosened to facilitate the removal of the respective shims, and the seal assembly subunit 82, the face seal 88 and the face seal body 89, held tightly within the seal assembly subunit 82, can be moved forward toward the concentric flange 83 and the inner face 87, a small distance. This movement allows the face seal lip 90 to be forced even more against the inner face 87, so that a first distance "X", between the face seal body 89 and the inner face 87, shown in FIGS. 11A and 11B, is diminished from the first distance to a second distance "B", shown in FIG. 13. The distance is diminished uniformly, thereby uniformly increasing the pressure on the face seal 88 and the inner face wear plate 86.

Figure 10:
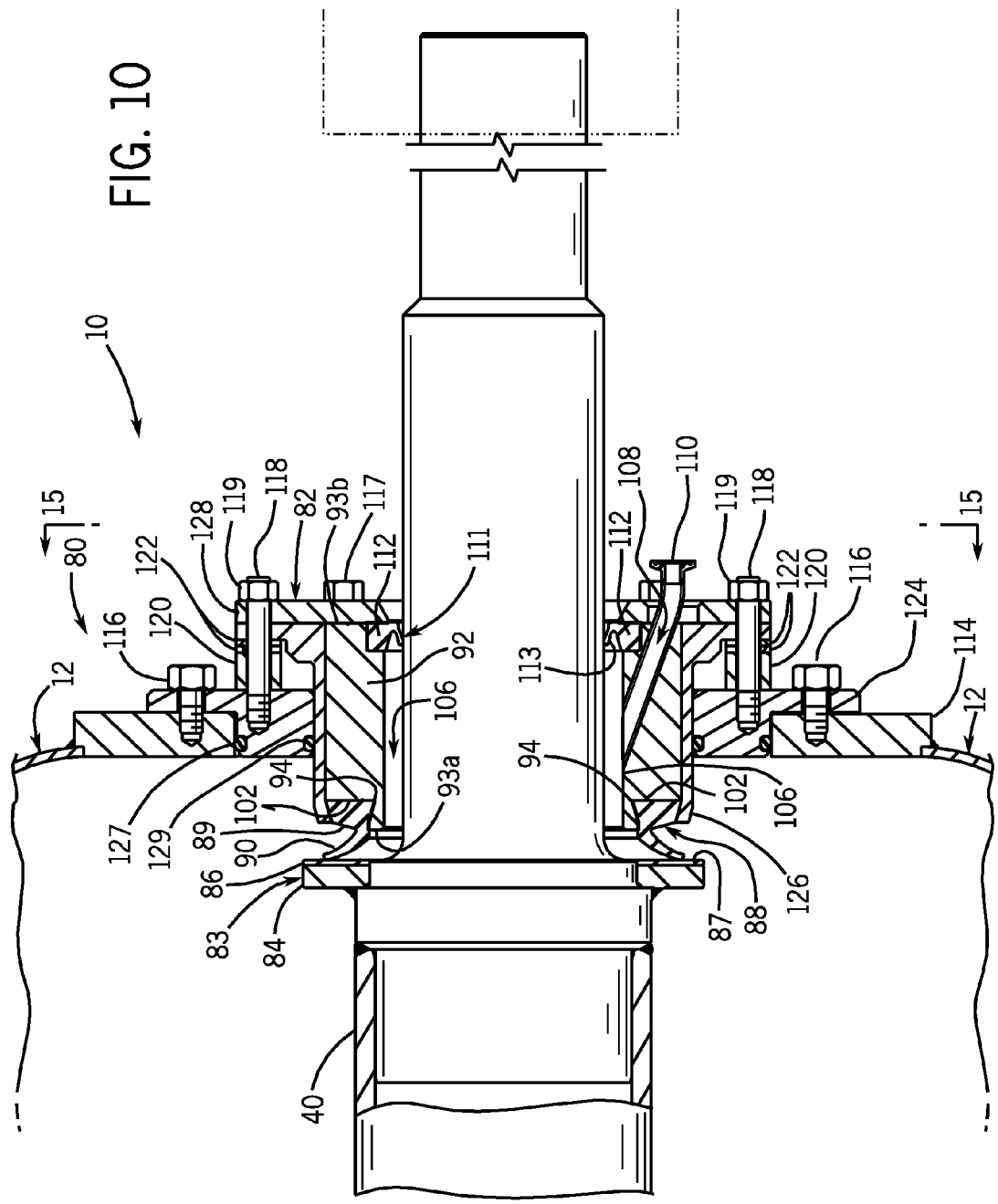
FIG. 10 is an enlarged partial cross-sectional side view of the preferred shaft seal assembly of the present invention shown in the area partially circumscribed by the line 10-10 of FIG. 6A.
Figure 14:
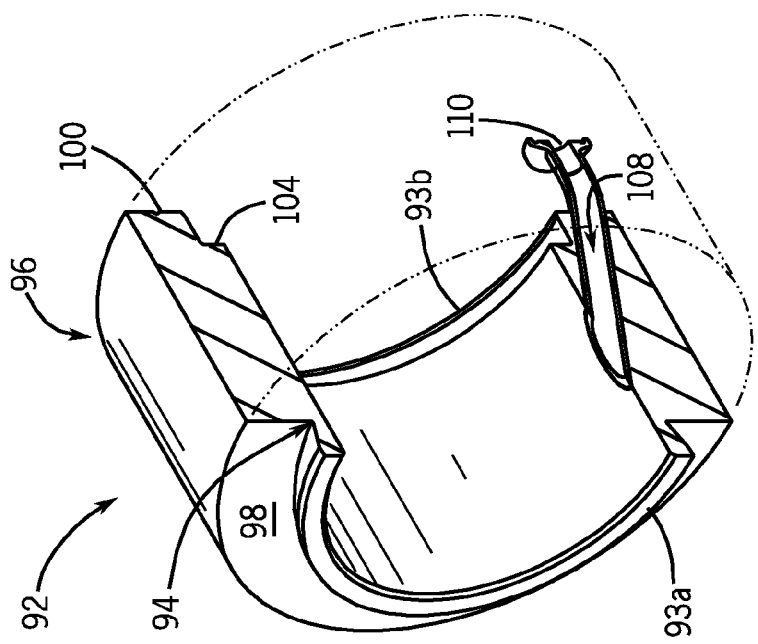
FIG. 14 is an enlarged partial cross-sectional, perspective view of the inner seal holder 92 of the shaft seal assembly of FIGS. 10, 11A, 11B, 12 and 13.

FIG. 14 illustrates a preferred inner seal holder 92 that partially defines the seal chamber 106 as shown in FIG. 10. The inner seal holder 92 has a cylindrical body 96 having a first edge 98 and a second edge 100. The first edge 98 includes a first groove 94. As shown in FIG. 10, the inner portion of the first groove 94 mates with a portion of the outer seal holder 126 to form a dovetail groove 102 in which the face seal body 89 of the face seal 88 is secured. The dovetail groove 102 is sized and configured to reflect the parameters of the face seal body 89, so that the face seal body 89 is only moderately compressed when the face seal 88 is placed in the first groove of the inner seal holder 92 and the outer seal holder 126 is forced over the face seal 88 and the inner seal holder 92. The second edge 100 of the inner seal holder 92 has a second groove 104 in which the shaft seal body 112 will be engaged. As also shown in FIG. 10, the shaft seal lip 113 is positioned in the second groove 104 in such a way the shaft seal body 112 is moderately compressed when the seal retaining plate 128 is tightened against the outer seal holder 126, the shims 122, the tubular spacers 120 and the inner face mounting flange 124.

Figure 15:
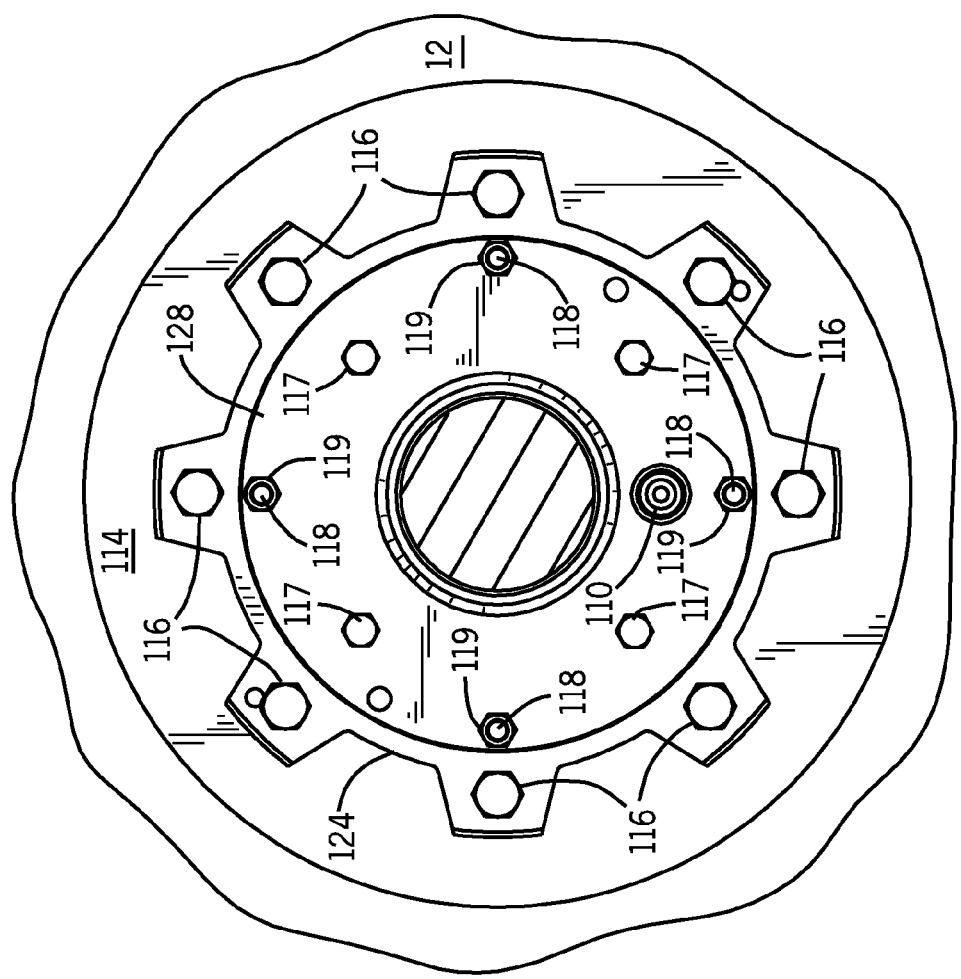
FIG. 15 is an enlarged partial cross-sectional, end view of the preferred seal assembly of the seal shown in FIG. 10 as seen from the line 15-15 of FIG. 10.

FIG. 15 is an end view of the second end 41 of the cheese process vat 10, showing an external portion of the shaft seal assembly 80 of FIGS. 10-12 showing a preferred arrangement of studs 118 and nuts 119 and screws 116, 117. This screw arrangement provides for a uniform tightening along the outer diameter of the inner mounting flange ring 124 and the stud/nut arrangement provides for a uniform tightening along the outer diameter of the seal assembly subunit 82, although numerous other arrangements may be used.

Example 1

Performance Testing: Testing whey from cheese making operations for remaining fat content in the whey is one of the most common tests used to compare cheese making efficiently, in different vats in cheese plants throughout the industry. The results are often used as a measure of performance. By testing the amount of fat in the whey, cheese plants can predict the performance of the cheese process vats. It is desirable to have as low a fat content in the whey as possible for each type of cheese.

Performance test results for whey from a single agitator shaft vat of the present invention were compared with test results for a well known dual agitator shaft vat.

The test procedure begins by collecting a small whey sample from the cheese process vat during the "predraw/settle" step. This sample of approximately 4 to 6 ounces is sent to a commercial laboratory where the sample is tested with a standard infrared spectroscopy test for fat quantity as a percentage fluid volume. The method used is a standard infrared analysis of the sample for the amount of fat, protein, lactose and total solids in the whey. A low fat content in the whey is generally believed to correlate with a higher cheese yield, which is clearly desirable to plant operators. The Whey Fat Test Results generated in this procedure are shown below in Table 1. The testing evaluation shows that the cheese process vat of the present invention is very competitive with the known dual vat system tested that is one of the more popular cheese process vats in the industry. In these test results, the cheese process vat of the present invention was lower in whey fats on 10 of the 12 days that were comparison test.

TABLE 2

The Percentage of Fat in Whey Determinations for Performance Testing in Example 1.
Percent of Fat in Whey

| Day Tested | Present Single Agitator Shaft Vat | Dual Agitator Shaft Vat |
| --- | --- | --- |
| Day 1 | 0.274% | 0.28% |
| Day 2 | 0.302% | 0.289% |
| Day 3 | 0.288% | 0.299% |
| Day 4 | 0.263% | 0.274% |
| Day 5 | 0.26% | 0.32% |
| Day 6 | 0.253% | 0.266% |
| Day 7 | 0.232% | 0.235% |
| Day 8 | 0.232% | 0.224% |
| Day 9 | 0.178% | 0.219% |
| Day 10 | 0.198% | 0.261% |
| Day 11 | 0.246% | 0.252% |
| Day 12 | 0.232% | 0.236% |
| Ave. (mean) | 0.247% | 0.263% |

It will be appreciated that the foregoing is only illustrative of the broad principles of the present invention. Furthermore, since numerous modifications and changes will readily occur to those skilled in the art, it is not desired to limit the invention to the exact construction and operation shown and described. While the preferred embodiment has been described herein, the details may be changed without departing from the intended scope of the invention, which is defined by the attached claims.

What is claimed is:

1. A cheese process vat having a fluid accessible cleaning/sanitizing chamber through which a cleaning/sanitizing fluid can be passed to clean/sanitize the cheese process vat during a cleaning/sanitizing process, the cheese process vat comprising:
   a vat body having an interior and first and second ends;
   a shaft assembly including a shaft extending between the first and second ends;
   the shaft including a concentric flange having an inner face; and
   a shaft seal assembly including a seal assembly subunit including an inner seal holder, a face seal and a shaft seal, each of which surround and are concentric with the shaft; wherein the shaft seal and the face seal are engaged with and separated by the inner seal holder; the face seal and the shaft seal each having a seal body and a seal lip; the seal lip extending away from the seal body; wherein the shaft seal is pre-loaded so that the shaft seal lip engages the shaft; the face seal is pre-loaded so that the face seal lip engages the inner face; the inner seal holder defines a first portion of a fluid conduit channel and the shaft, the inner seal holder, the face seal and the shaft seal cooperate to define a fluid accessible cleaning/sanitizing chamber to which cleaning/sanitizing solution can flow via the first portion of the fluid conduit channel.

2. The cheese process vat of claim 1, further comprising a cleaning/sanitizing solution inlet, wherein the inner seal holder at least partially defines the fluid conduit channel; wherein the cleaning/sanitizing chamber can communicate with the cleaning/sanitizing solution inlet via the fluid conduit channel.

3. The cheese process vat of claim 2, wherein the face seal is made of a resilient elastomeric material that is sufficiently flexible to permit the face seal lip to deform to allow cleaning/sanitizing solution to flow between the face seal lip and the inner face to enter into the interior of the vat body via the cleaning/sanitizing chamber and the fluid conduit channel when the cleaning/sanitizing solution is introduced into the cleaning/sanitizing solution inlet under pressure.

4. The cheese process vat of claim 3, wherein the face seal is made of a sanitary synthetic rubber product.

5. The cheese process vat of claim 3, wherein the vat body includes a drainage port that communicates with the interior of the vat body and the cheese process vat is constructed and arranged so that any cleaning/sanitizing solution introduced into the interior of the vat body will drain out of the interior via the drainage port.

6. The cheese process vat of claim 3, wherein the outer seal holder and the inner seal holder cooperate to create a dovetail groove in which the face seal is engaged.

7. The cheese process vat of claim 6, wherein the face seal is engaged by the outer seal holder and the inner seal holder such that the face seal lip places a pre-loaded pressure against the inner face.

8. The cheese process vat of claim 1, wherein the shaft seal assembly further includes an outer seal holder and the outer seal holder cooperates with the inner seal holder to engage the face seal.

9. The cheese process vat of claim 1, wherein the shaft seal assembly further includes a seal retaining plate and the seal retaining plate cooperates with the inner seal holder to engage the shaft seal.

10. The cheese process vat of claim 9, wherein the shaft seal is engaged by the inner seal holder and the seal retaining plate such that the shaft seal lip places a pre-loaded pressure against the shaft.

11. The cheese process vat of claim 1, wherein the fluid accessible cleaning/sanitizing chamber encircles the shaft so that the cleaning/sanitizing solution can flow around the shaft.

12. The cheese process vat of claim 1, wherein the shaft and the inner seal holder are made of stainless steel.

13. The cheese process vat of claim 1, wherein the face seal and the shaft seal are made of a resilient elastomeric material.

14. The cheese process vat of claim 13, wherein the face seal and the shaft seal are made of a resilient sanitary synthetic rubber product.

15. A cheese process vat having a fluid accessible cleaning/sanitizing chamber through which a cleaning/sanitizing solution can be passed to sanitize the cheese process vat during a cleaning/sanitizing process, the cheese process vat comprising:
a vat body having an interior and first and second ends;
a shaft assembly including a shaft extending between the first and second ends;
the shaft including a concentric flange having an inner face; and
a shaft seal assembly including a seal assembly subunit including an inner seal holder, a face seal, a shaft seal, an outer seal holder and a seal retaining plate, each of which surround and are concentric with the shaft; wherein the shaft seal and the face seal are engaged with and separated by the inner seal holder; wherein the inner seal holder defines a first portion of a fluid conduit channel and the shaft, the inner seal holder, the face seal and the shaft seal cooperate to define a fluid accessible cleaning/sanitizing chamber to which cleaning/sanitizing solution can flow via the first portion of the fluid conduit channel.

16. The cheese process vat of claim 15, further comprising a cleaning/sanitizing solution inlet, wherein the inner seal holder at least partially defines the fluid conduit channel; wherein the cleaning/sanitizing chamber can communicate with the cleaning/sanitizing solution inlet via the fluid conduit channel.

17. The cheese process vat of claim 16, wherein the face seal and the shaft seal each having a seal body and a seal lip, each seal lip extending away from the seal body; wherein the shaft seal is pre-loaded so that the shaft seal lip engages the shaft; the face seal is pre-loaded so that the face seal lip engages the inner face; wherein the face seal is made of a resilient elastomeric material that is sufficiently flexible to permit the face seal lip to deform to allow cleaning/sanitizing solution to flow between the face seal lip and the inner face and enter into the interior of the vat body via the cleaning/sanitizing chamber and the fluid conduit channel when the cleaning/sanitizing solution is introduced into the cleaning/sanitizing solution inlet under pressure.

18. The cheese process vat of claim 17, wherein the face seal is made of a sanitary synthetic rubber product.

19. The cheese process vat of claim 17, wherein the vat body includes a drainage port that communicates with the interior of the vat body and the cheese process vat is constructed and arranged so that any cleaning/sanitizing solution introduced into the interior of the vat body will drain out of the interior via the drainage port.

20. The cheese process vat of claim 1, wherein the fluid accessible cleaning/sanitizing chamber encircles the shaft so that the cleaning/sanitizing solution can flow around the shaft.

21. The cheese process vat of claim 15, wherein the shaft and the inner seal holder are made of stainless steel.

22. The cheese process vat of claim 15, wherein the face seal and the shaft seal are made of a resilient elastomeric material.

23. The cheese process vat of claim 22, wherein the face seal and the shaft seal are made of a sanitary synthetic rubber product.

* * * * *